(12) United States Patent  (10) Patent No.: US 8,711,360 B2
Funamoto  (45) Date of Patent: Apr. 29, 2014

(54) SPECTRAL MEASUREMENT DEVICE

(71) Applicant: Seiko Epson Corporation, Tokyo (JP)

(72) Inventor: Tatsuaki Funamoto, Shiojiri (JP)

(73) Assignee: Seiko Epson Corporation (JP)

( * ) Notice: Subject to any disclaimer, the term of this patent is extended or adjusted under 35 U.S.C. 154(b) by 0 days.

(21) Appl. No.: 13/948,753

(22) Filed: Jul. 23, 2013

(65) Prior Publication Data

US 2013/0311125 A1 Nov. 21, 2013

Related U.S. Application Data

(62) Division of application No. 13/112,401, filed on May 20, 2011.

(30) Foreign Application Priority Data

Jun. 22, 2010 (JP) ................................ 2010-141229

(51) Int. Cl.
*G01B 9/02* (2006.01)
*G01J 3/42* (2006.01)

(52) U.S. Cl.
USPC ........... 356/451; 356/452; 356/453; 356/454; 356/455; 356/456; 356/319; 356/320; 356/321; 356/322; 356/323; 356/324; 356/325

(58) Field of Classification Search
USPC .................................. 356/319–325, 451–456
See application file for complete search history.

(56) References Cited

U.S. PATENT DOCUMENTS

| 5,175,697 | A | 12/1992 | Kawagoe et al. |
| 5,774,213 | A * | 6/1998 | Trebino et al. ................ 356/320 |
| 6,785,002 | B2 | 8/2004 | Zarrabian et al. |
| 6,844,930 | B2 | 1/2005 | Kobayashi et al. |
| 7,825,371 | B2 | 11/2010 | Ruan et al. |
| 2012/0044491 | A1 | 2/2012 | Urushidani et al. |

FOREIGN PATENT DOCUMENTS

| JP | 05-248952 | 9/1993 |
| JP | 2001-108613 A | 4/2001 |
| JP | 2002-277326 A | 9/2002 |

OTHER PUBLICATIONS

Endo, T., "Spatial estimation of biochemical parameters of leaves with hyperspectral imager" Proceedings. 22nd Asian Conference on Remote Sensing (ACRS), 2001 (6 pages).

* cited by examiner

*Primary Examiner* — Tarifur Chowdhury
*Assistant Examiner* — Sunghee Y Gray
(74) *Attorney, Agent, or Firm* — Harness, Dickey & Pierce, P.L.C.

(57) ABSTRACT

A spectral measurement device includes: an optical band-pass filter section that has first to n-th wavelengths (n is an integer of 2 or more) having a predetermined wavelength width as a spectral band thereof; a correction operation section that corrects a reception signal based on an output optical signal from the optical band-pass filter section; and a signal processing section that executes predetermined signal processing based on the reception signal corrected by the correction operation section that corrects the reception signal based on the change in the spectral distribution of the reception signal.

6 Claims, 19 Drawing Sheets

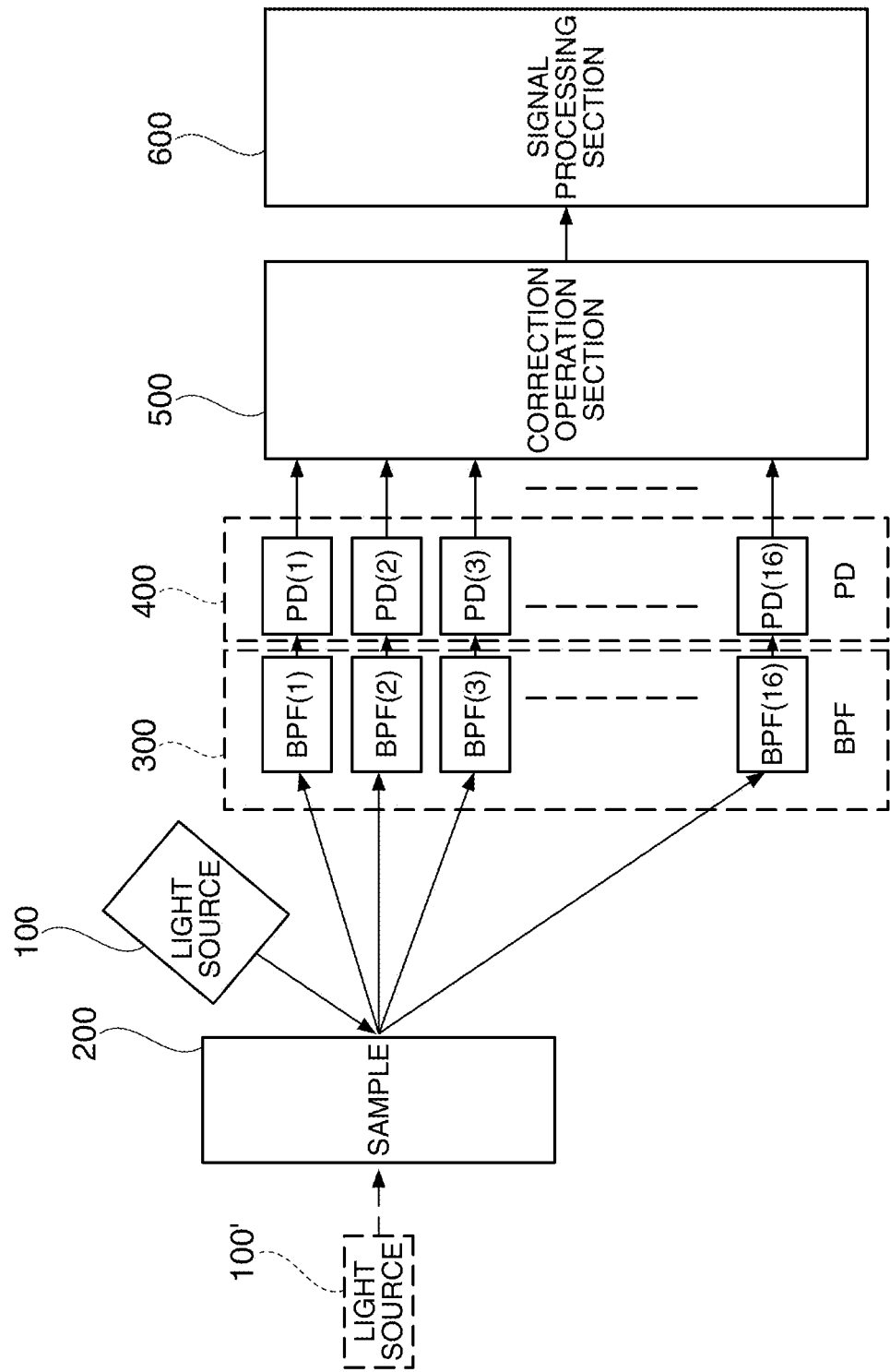

3' IS EXTRACTED

FIG. 14A RELATIVE SPECTRAL INTENSITY DISTRIBUTION OF RECEPTION SIGNAL CORRESPONDING TO BPF(3)
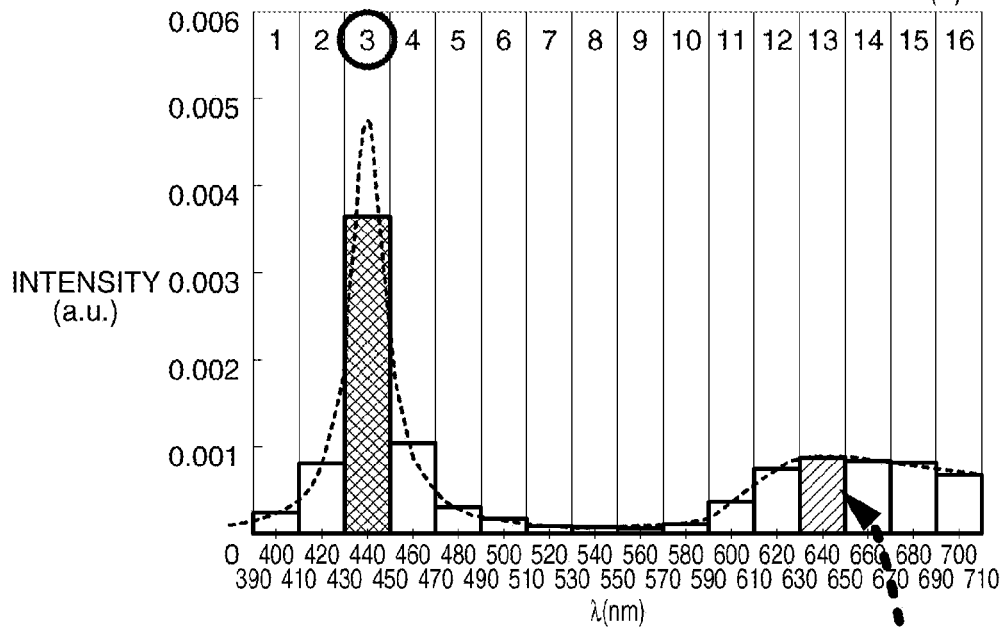
FIG. 14B RELATIVE SPECTRAL INTENSITY DISTRIBUTION OF RECEPTION SIGNAL CORRESPONDING TO BPF(13)
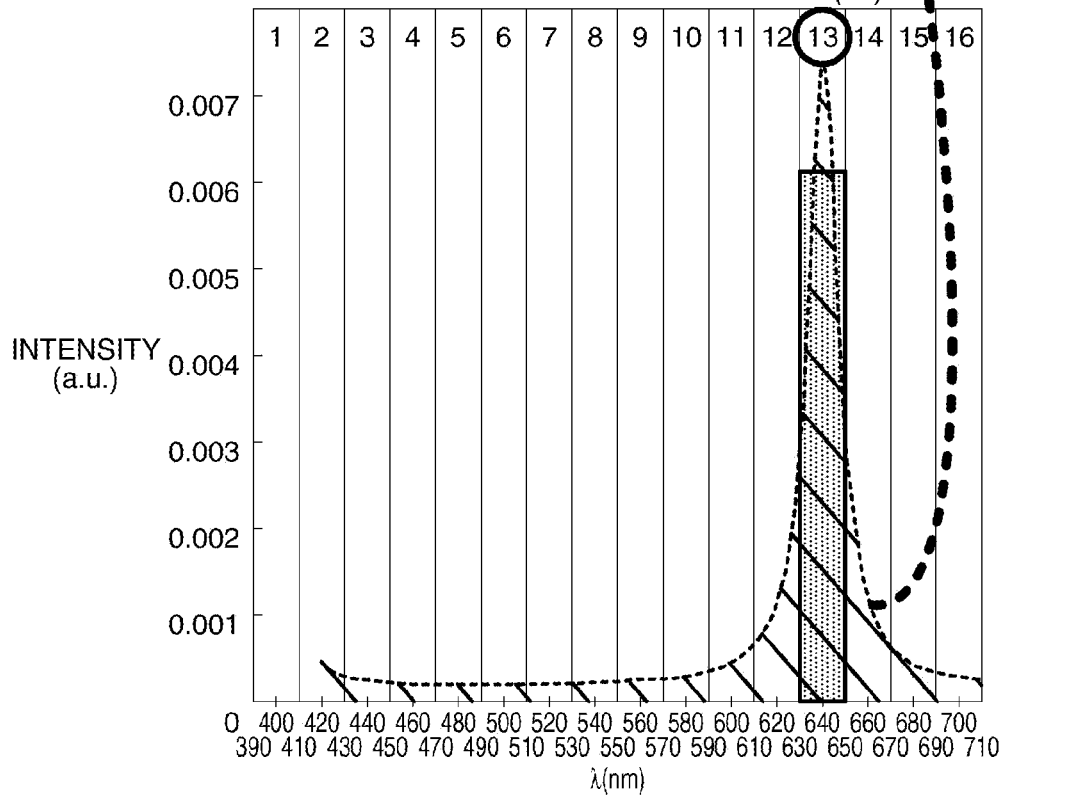

FIG. 15A

BPF(13)
(BAND-PASS FILTER OF 640-nm BAND)

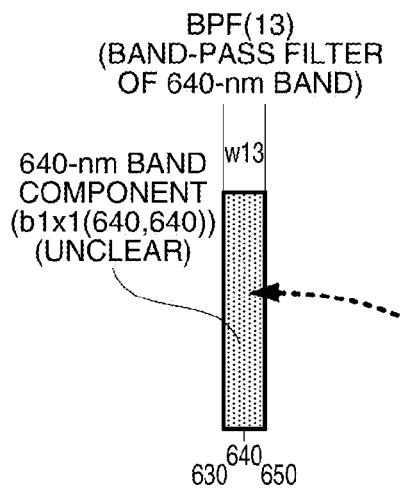

640-nm BAND COMPONENT
(b1x1(640,640))
(UNCLEAR)

Fbps13($\lambda$=640)(KNOWN)
TRANSMITTANCE IN 640-nm BAND (w13) of BPF(13)
(=TRANSMITTANCE IN 640 nm)

INTEGRATED VALUE OF DETECTION CURRENT OF PD(13) (KNOWN)
(Ix($\lambda$=640nm))

FIG. 15B

BPF(3)
(BAND-PASS FILTER OF 440-nm BAND)

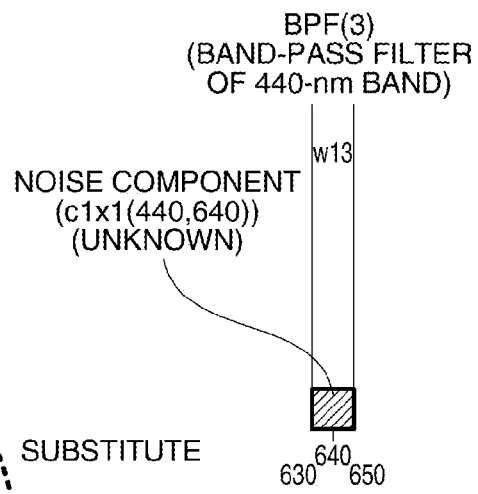

NOISE COMPONENT
(c1x1(440,640))
(UNKNOWN)

SUBSTITUTE

Fbps3($\lambda$=640)(KNOWN)
=$\Sigma$(Fbps($\lambda$=630)···Fbps($\lambda$=650))
(TRANSMITTANCE IN 640-nm BAND (w13) OF BPF(3))
(=AVERAGE OVER THE WAVELENGTHS 630 nm TO 650 nm)

FIG. 15C

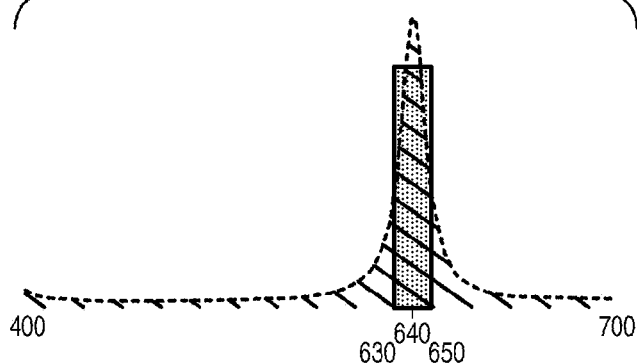

FIG. 15D

NOISE COMPONENT(c1x1(440,640)) $\approx$ Ix($\lambda$=640nm) $\times \dfrac{Fbps3(\lambda=640)}{Fbps13(\lambda=640)}$ ·····(1)

FIG. 16A

Fbps3(380~780)
(INTEGRATED VALUE OF TRANSMITTANCE IN ALL OF THE BANDS OF BPF(3))

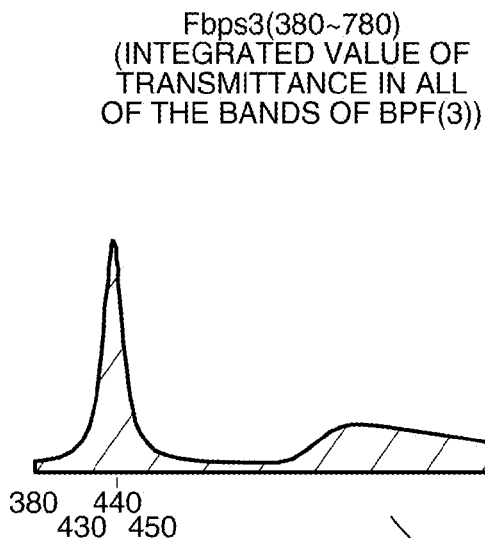

Fbps13(380~780)
(INTEGRATED VALUE OF TRANSMITTANCE IN ALL OF THE BANDS OF BPF(13))

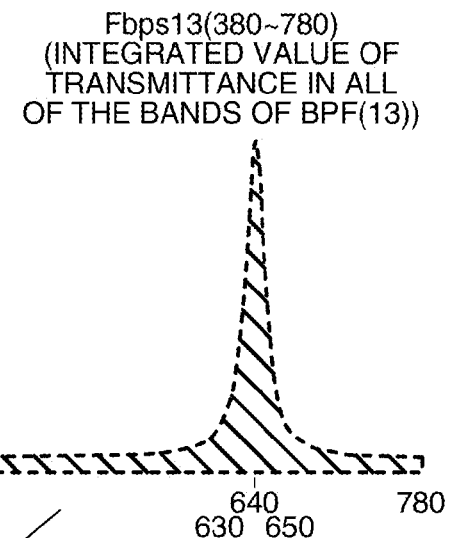

380         630 640 650   780

THE TOTAL INTENSITIES OF LIGHT AFTER PASSING THROUGH THE RESPECTIVE FILTERS ARE DIFFERENT.

FIG. 16C

NOISE COMPONENT
($c1 \times 1(440,640)$)

$$\approx Ix(\lambda=640nm) \times \left(\frac{Fbps3(380\sim780)}{Fbps13(380\sim780)}\right) \times \frac{Fbps3(\lambda=640)}{Fbps13(\lambda=640)} \quad \cdots (3)$$

R
(TRANSMITTANCE CORRECTION COEFFICIENT)

FIG. 17A

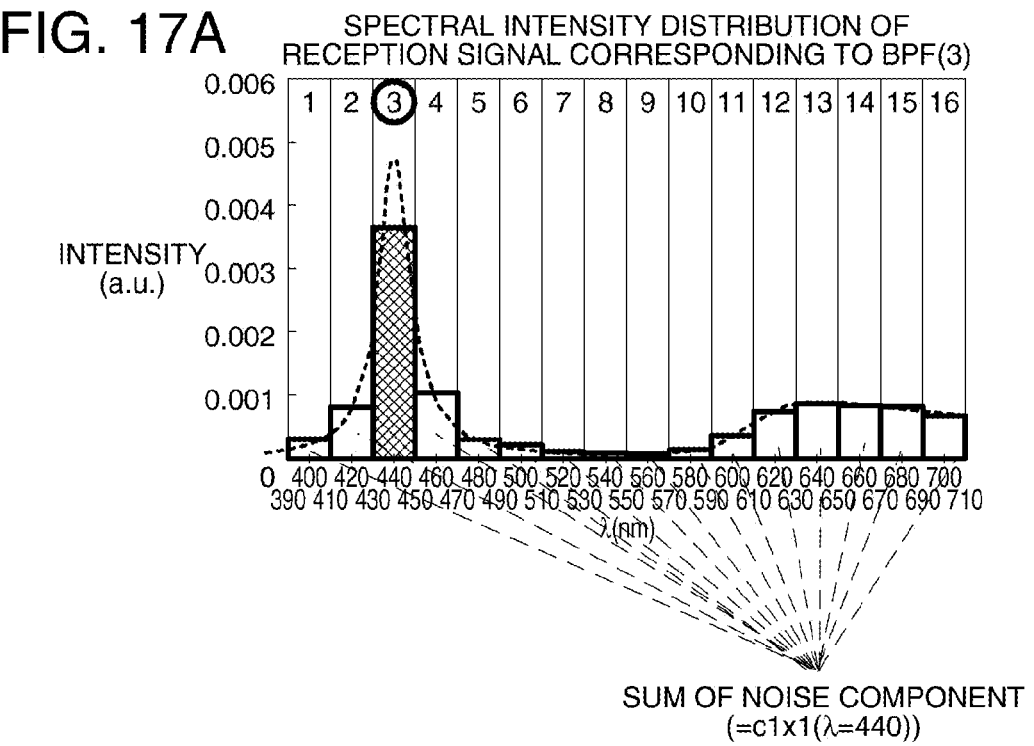

SUM OF NOISE COMPONENT
(=c1×1(λ=440))

FIG. 17B

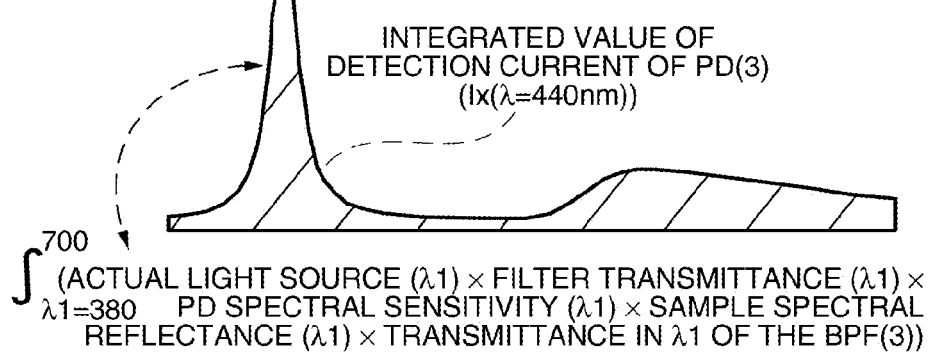

$$\int_{\lambda 1=380}^{700} (\text{ACTUAL LIGHT SOURCE }(\lambda 1) \times \text{FILTER TRANSMITTANCE }(\lambda 1) \times \text{PD SPECTRAL SENSITIVITY }(\lambda 1) \times \text{SAMPLE SPECTRAL REFLECTANCE }(\lambda 1) \times \text{TRANSMITTANCE IN }\lambda 1 \text{ OF THE BPF(3)})$$

FIG. 17C

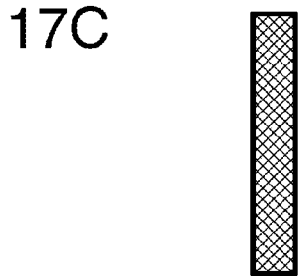

CORRECTED DETECTION SIGNAL OF 440-nm BAND (=cr(Ix(3))
(INTEGRATED VALUE OF DETECTION CURRENT OF PD(3))
-k1·(SUM OF NOISE COMPONENTS)

SPECTRAL INTENSITY DISTRIBUTION OF BPF(3)

Ftc(APPARENT PROPERTIES OF BPF(3) CONSIDERING CORRECTION OPERATION)

Ftr(ACTUAL PROPERTIES OF BPF(3))

SPECTRAL MEASUREMENT DEVICE

CROSS REFERENCE TO RELATED APPLICATIONS

This is a divisional application of U.S. application Ser. No. 13/112,401 filed May 20, 2011 which claims priority to Japanese Patent Application No. 2010-141229 filed Jun. 22, 2010 all of which are incorporated by reference herein in their entireties.

BACKGROUND

1. Technical Field

The present invention relates to spectral measurement devices and the like.

2. Related Art

Examples of a spectral measurement device include a colorimeter, a spectroscopic analyzer, and a spectrum analyzer. JP-A-2002-277326 discloses a spectral measurement device that uses a transmission wavelength-variable filter. Moreover, JP-A-5-248952 discloses an optical spectrum analyzer that uses an etalon spectrometer (Fabry-Perot etalon filter) as a spectrometer capable of variably controlling transmission wavelengths.

In a spectral measurement device that uses an optical band-pass filter (having a plurality of spectral bands), the reception signal intensities of the respective spectral bands can be calculated by integrating (summing) the reception light intensity for each wavelength included in the respective spectral bands. For example, by using the integrated value (summed value) as the reception light intensity corresponding to the central wavelengths of the respective spectral bands, it is possible to obtain spectral reception light intensity data for each spectral band.

However, for example, when the optical spectrum (reception light intensity distribution for each wavelength) of a sample changes abruptly, the measurement error (integration error) increases. In order to reduce the measurement error, it is effective to increase the number of spectral bands to set the wavelength widths of the respective spectral bands so as to be as narrow as possible. However, in this case, the spectrometer (for example, the optical band-pass filter) becomes too large, and it is necessary to use an expensive spectrometer. Therefore, for example, when reduction of the costs and size of the spectral measurement device is prioritized, it is difficult to use the high-performance optical band-pass filters.

SUMMARY

An advantage of some aspects of the invention is that it provides a spectral measurement device capable of improving measurement accuracy without using an expensive optical band-pass filter, for example.

(1) According to an aspect of the invention, there is provided a spectral measurement device including: an optical band-pass filter section that has first to n-th wavelengths (n is an integer of 2 or more) having a predetermined wavelength width as a spectral band thereof; a light receiving section that receives light from the optical band-pass filter section; a correction operation section that performs an operation to correct a reception signal obtained from the light receiving section; and a signal processing section that executes predetermined signal processing based on the reception signal corrected by the correction operation section, wherein the correction operation section corrects the reception signal based on a change in a spectral distribution of the reception signal.

When the curvature (the degree of curvedness) of a characteristic line (which may be a straight line or a curve, and is sometimes referred to as a spectral distribution curve) representing an optical spectrum (a reception light intensity distribution for each wavelength) changes abruptly, particularly, a difference between an integrated value of reception light intensities for each wavelength of the spectral band and an actual reception light intensity at the central wavelength of the spectral band increases.

Therefore, in this aspect of the invention, the correction operation section corrects the reception signal (reception data) based on a change in the spectral distribution of the reception signal. In this way, measurement errors (measurement errors resulting from the change in the spectral distribution: integration errors) are suppressed.

For example, the reception signal can be corrected by superimposing (adding or subtracting) a correction value on the reception signal. Moreover, the reception signal can be also corrected by multiplying the reception signal by the correction value (correction coefficient). The measurement error is reduced by the correction operation. Therefore, it is possible to perform high-accuracy spectral measurement, for example, by using an optical filter (variable wavelength filter and the like) which has good usability and is relatively cheap and small.

(2) According to another aspect of the invention, in the spectral measurement device, the correction operation section calculates a second derivative of a spectral distribution curve representing the spectral distribution of the reception signal, decreases the value of the reception signal through the correction when the second derivative is positive, and increases the value of the reception signal through the correction when the second derivative is negative.

The degree of the change in the curvature of the spectral distribution curve (plane curve) and whether the spectral distribution curve is an upwardly convex curve or a downwardly convex curve can be detected by the second derivative of the spectral distribution curve. Therefore, the correction operation section generates a correction value based on the second derivative of the spectral distribution curve and corrects the reception signal (reception data or reception light intensity data) using the generated correction value.

For example, when the polarity of the second derivative of the spectral distribution (spectral intensity distribution, spectral distribution curve) of the reception signal is positive, the spectral distribution curve is a downwardly convex curve. In this case, an integrated value of the spectral intensities for each wavelength of one spectral band tends to be larger than the actual reception light intensity at the central wavelength of the spectral band. Therefore, when the second derivative is positive, the value of the reception signal (reception data) is decreased by correction so as to suppress errors. On the other hand, when the polarity of the second derivative is negative, the spectral distribution curve is an upwardly convex curve. In this case, an integrated value of the spectral intensities for each wavelength of one spectral band tends to be smaller than the actual reception light intensity at the central wavelength of the spectral band. Therefore, when the second derivative is negative, the value of the reception signal (reception data) is increased by correction so as to suppress errors.

Moreover, a predetermined fixed value may be used as the correction value, and a correction value (variable correction value) of which the value changes in accordance with the degree of the change in the spectral distribution curve may be used. Furthermore, when a variable correction value is used, a method in which the value of the correction value is continuously changed in accordance with the degree of the change in the spectral distribution may be used. Alternatively, a method in which the degree of the change in the spectral distribution may be divided into a plurality of steps using a threshold or the like, and the value of the correction value is changed (switched) gradually in accordance with the respective steps may be used. Moreover, the second derivative can be calculated by a simple operation which uses the measurement data of three adjacent wavelength bands, for example. Furthermore, a plane curve (approximated curve) may be estimated based on the actual measurement values (discrete values), and the second derivative of the plane curve may be calculated.

(3) According to another aspect of the invention, in the spectral measurement device, the correction operation section controls a correction value used for the correction variably based on the magnitude of an absolute value of the second derivative.

The measurement error decreases when the change in the curvature of the spectral distribution curve is smooth and increases when the change is abrupt. That is, the measurement error correlates with the curvature of the spectral distribution curve. Here, the degree of the change in the curvature of the spectral distribution curve can be determined based on the magnitude of the absolute value of the second derivative. Therefore, in this aspect of the invention, the correction operation section controls the correction value variably based on the magnitude of the absolute value of the second derivative. For example, when the curvature of the spectral distribution curve changes abruptly, the value of the correction value is adjusted variably so that the amount of correction of the reception signal by the correction value is larger than that when the change is smooth. In this way, the correction accuracy is improved further.

(4) According to another aspect of the invention, in the spectral measurement device, when a reception light intensity of a first spectral band is p1, a reception light intensity of a second spectral band adjacent to the first spectral band is p2, and a reception light intensity of a third spectral band adjacent to the second spectral band is p3, the correction operation section calculates a second derivative Q1 through an operation based on $Q1=(p1+p3-2 \cdot p2)$ and calculates a correction value used for the correction of the reception light intensity p2 of the second spectral band by multiplying the calculated second derivative Q1 by a correction coefficient k1 (k1 is a real number).

In this aspect of the invention, the second derivative is calculated by a simple operation using the actual measurement data p1, p2, and p3 (3-point data) for each of three adjacent spectral bands (first to third spectral bands). Moreover, the second derivative is used for generation of the correction value.

When the polarity of the second derivative Q1 ($=p1+p3-2 \cdot p2$) is positive, the spectral distribution curve is a downwardly convex curve. When the polarity is negative, the spectral distribution curve is an upwardly convex curve. When the second derivative Q1 is 0, the spectral distribution changes in a straight line. Moreover, when the curvature of the spectral distribution curve is large (the change in the spectral intensity is abrupt), the actual measurement data p3 increases. As a result, the absolute value of the second derivative Q1 increases.

That is, the second derivative Q1 (positive or negative) serves as information on the shape of the spectral distribution curve (information on whether the curve is upwardly convex or downwardly convex) and information on the abruptness of the change in the curvature of the spectral distribution.

Focusing on this property, in this aspect of the invention, the second derivative Q1 is used as the basic data for calculation of the correction value, and the second derivative Q1 is multiplied by a correction coefficient k1 (k1 is a real number) (that is, the magnitude thereof is appropriately adjusted), and the result of multiplication is used as the correction value. If k1=1, the second derivative Q1 is used as the correction value as it is. Moreover, although the correction coefficient k1 is basically a positive real number excluding 0, k1 may exceptionally be set to 0 (for example, when no correction is executed). According to this method, the correction value of which the magnitude is variably controlled can be generated quickly (for example, real-time) by a simple method (simple configuration).

(5) According to another aspect of the invention, in the spectral measurement device, that when, among the first to n-th wavelengths, an m-th wavelength band ($1 \leq m \leq n$, and m is an integer) is an interest wavelength band, and a k-th wavelength band ($k \neq m$, $1 \leq k \leq n$, and k is an integer) other than the m-th wavelength band is a non-interest wavelength band, the optical band-pass filter section functions as an m-th band-pass filter corresponding to the m-th wavelength band and also functions as a k-th band-pass filter corresponding to the k-th wavelength band, the correction operation section further includes a noise estimation section that estimates the amount of the noise component for each wavelength band of the k-th wavelength band included in an interest reception signal obtained by the light receiving section receiving transmission light or reflection light of the m-th band-pass filter corresponding to the m-th wavelength band, and a noise removal and correction section that performs correction of subtracting the sum of the estimated noise component for each wavelength band from the interest reception signal, and the correction operation section executes correction of the reception signal by the noise estimation section and the noise removal and correction section and then executes the correction based on the change in the spectral distribution of the reception signal.

In this aspect of the invention, in addition to the integration error correction (correction which mainly aims to suppress spreading of errors at positions where the change in the spectral distribution curve is large), by executing a correction operation (base floating correction) for suppressing a noise component (component of wavelengths other than a desired wavelength band) superimposed on the spectroscopic data, more highly accurate correction is achieved.

The optical band-pass filter section used as a spectrometer (optical filter) functions as a m-th band-pass filter corresponding to an m-th wavelength band ($1 \leq m \leq n$) which is an interest wavelength band and a k-th band-pass filter corresponding to a k-th wavelength band ($k \neq m$ and $1 \leq k \leq n$) which is a non-interest wavelength band. When the half bandwidth of the optical band-pass filter is broad, a component of wavelengths other than a desired wavelength band is mixed, and the reception signal level increases by an amount corresponding to the component. Thus, a base floating error occurs.

Therefore, in this aspect of the invention, a correction operation (base floating correction) is executed in which the sum of the noise component for each wavelength band included in all of the reception signals (that is, interest reception signals) obtained by receiving light from the m-th band-pass filter, and the calculated sum of noise components is subtracted from all of the reception signals to thereby suppress the effect of noise. This base floating correction is preferably executed prior to the integration error correction. That is, noise is removed from the spectroscopic data of the respective spectral bands (spectral wavelength bands)

through the base floating correction, and the integration error correction is executed based on the spectroscopic data in which the noise is removed. Thus, the correction accuracy can be further improved.

Moreover, a noise estimation section and a noise removal and correction section are provided as a configuration for the base floating correction. The noise estimation section estimates the amount of the noise component for each wavelength band of the k-th wavelength band included in an interest reception signal obtained by the light receiving section receiving transmission light or reflection light of the m-th band-pass filter corresponding to the m-th wavelength band. Moreover, the noise removal and correction section performs correction of subtracting the sum of the estimated noise component for each wavelength band from the interest reception signal to thereby calculate a corrected reception signal. By executing the base floating suppressing correction, it is possible to further improve the accuracy of the spectroscopic data (optical spectrum data). Therefore, it is possible to achieve further improvement in the measurement accuracy of the spectral measurement device.

As a transmission-type optical band-pass filter, an etalon filter can be used, for example, and as a reflection-type optical band-pass filter, a dichroic mirror can be used, for example. The first to n-th optical band-pass filters corresponding to the respective wavelength bands may be realized using a variable wavelength filter and may be realized by juxtaposing a plurality (n) of fixed wavelength filters having different wavelength bands.

(6) According to another aspect of the invention, in the spectral measurement device, when the interest reception signal obtained by the light receiving section receiving the transmission light or reflection light of the m-th band-pass filter is Sm, a non-interest reception signal obtained by the light receiving section receiving the transmission light or reflection light of the k-th band-pass filter is Sk, a transmittance or a reflectance in the k-th wavelength band of the m-th band-pass filter is P(m,k), a transmittance or a reflectance in the k-th wavelength band of the k-th band-pass filter is P(k,k), and a noise component for each wavelength band of the k-th wavelength band included in the interest reception signal Sm is N(m,k), the noise estimation section performs an operation based on Formula (1) (N(m,k)=Sk·{P(m,k)/P(k,k)}(1)) to estimate the amount of the noise component for each wavelength band of the k-th wavelength band included in the interest reception signal Sm, and the noise removal and correction section calculates the sum ΣN(m,k) of the estimated noise component N(m,k) for each wavelength band and executes an operation based on Formula (2) (Smc=Sm−ΣN(m,k)(2)) to obtain the corrected reception signal Smc.

In this aspect of the invention, an example of base floating correction is made clear. That is, in this aspect of the invention, the noise estimation section estimates the amount of the noise component for each wavelength band in the non-interest wavelength band through the operation based on Formula (1). Moreover, the noise removal and correction section calculates the sum of the estimated noise components for each wavelength band and calculates the corrected interest reception signal (that is, corrected reception signal) through the operation based on Formula (2).

In Formula (1) above (that is, N(m,k)=Sk·{P(m,k)/P(k,k)}), Sk is the non-interest reception signals obtained by the light receiving section receiving the transmission light or the reflection light of the k-th band-pass filter. The non-interest reception signals are all of the reception signals which are the entire output of the photodiodes and are known since they are actually measured. Here, although it is ideal to use only the value of a reception signal corresponding to light of the k-th wavelength band among the non-interest reception signals, since it is not possible to separate only the reception component corresponding to the light of the k-th wavelength band, all of the reception signals of the k-th band-pass filter are used as a substitute.

Moreover, P(m,k) is the transmittance or the reflectance in the k-th wavelength band of the m-th band-pass filter. The notation P(m,k) represents the transmittance (or the reflectance) P in the "k"-th wavelength band which is the non-interest wavelength band, of the "m"-th band-pass filter (an optical filter associated with the "m"-th wavelength band which is the interest wavelength). Moreover, the spectral properties (relative spectral intensities of the respective wavelengths) in the all of the wavelength bands of the m-th band-pass filter are known. Moreover, P(m,k) can be calculated by integrating the transmittance (reflectance) of the respective wavelengths included in the k-th wavelength band (that is, by calculating all of the area of the k-th wavelength band in a graph showing the relationship between wavelengths and transmittance (reflectance)). Therefore, P(m,k) is known.

Moreover, P(k,k) is the transmittance or the reflectance in the k-th wavelength band of the k-th band-pass filter. The notation P(k,k) represents the transmittance (or the reflectance) P in the "k"-th wavelength band which is the non-interest wavelength band, of the "k"-th band-pass filter (an optical filter associated with the "k"-th wavelength band which is the non-interest wavelength). Moreover, since the k-th band-pass filter is a filter associated with the k-th wavelength band, the transmittance in the k-th wavelength band is known.

The interest reception signal Sm is calculated using these known values. That is, the noise components for each wavelength band of the k-th wavelength band included in all of the reception signals obtained by the light receiving section receiving light from the m-th band-pass filter which is a filter associated with the interest wavelength band are calculated. The use of the expression "noise components N(m,k) for each wavelength band of the k-th wavelength band" is based on the following reason. As described above, the first to n-th wavelength bands are wavelength bands each having a predetermined wavelength width, and if n≥3, there will be two or more k-th wavelength bands which are the non-interest wavelength bands. Considering this, the expression expresses a case in which when there is a plurality of wavelength bands as the non-interest wavelength bands, the noise components for each wavelength band are calculated.

Here, it is possible to obtain the reception signal Sk corresponding to the transmittance (reflectance) P(k,k) in the k-th wavelength band of the k-th band-pass filter. That is, all of the reception signals can be taken to be a substitute by regarding them as the reception signal corresponding to the k-th wavelength band. If P(k,k) is changed to P(m,k), since the amount of reception signals changes in accordance with the ratio between P(k,k) and P(m,k), the amount of reception signals will be changed to Sk·{P(m,k)/P(k,k)}. This amount of reception signal is regarded as the noise components N(m,k) for each wavelength band of the k-th wavelength band included in the interest reception signal Sm. Formula (1) above expresses this.

In this way, when the noise components are calculated for each non-interest wavelength band, the noise removal and correction section calculates the sum ΣN(m,k) of the estimated noise components N(m,k) for each wavelength band. The notation ΣN(m,k) represents the entire signal components (that is, all of the noise components ΣN) of the "k"-th wavelength band which is the non-interest wavelength band, included in all of the reception signals obtained by the light receiving section receiving light from the "m"-th band-pass filter which is a filter associated with the interest wavelength band.

Moreover, the noise removal and correction section executes an operation based on Formula (2) (namely, Smc=Sm−ΣN(m,k)) to obtain the corrected reception signal Smc. The corrected reception signal Smc is obtained by removing noise therefrom and can be regarded as substantially the reception signal corresponding to light of the interest wavelength band. Thus, the measurement accuracy of the optical spectrum data is improved.

(7) According to another aspect of the invention, in the spectral measurement device, when the sum of transmittance or reflectance of all of the wavelength bands of the m-th band-pass filter is ΣQm(1~n), the sum of transmittance or reflectance of all of the wavelength bands of the k-th band-pass filter is ΣQk(1~n), and a correction coefficient for correcting a difference in the transmittance properties or reflectance properties between filters is R (=ΣQm(1~n)/ΣQk (1~n)), the noise estimation section performs an operation based on Formula (3) (N(m,k)=Sk·{P(m,k)/P(k,k)}·R(3)) to estimate the amount of the noise component for each wavelength band of the k-th wavelength band included in the interest reception signal Sm.

In this aspect of the invention, another example of base floating correction (an example in which the accuracy of noise estimation is further increased) is made clear. That is, in this aspect of the invention, when calculating the noise components, Formula (3) is used in place of Formula (1) described above.

In the aspect (6) described above, noise components are calculated based on a way of thinking in which "if P(k,k) is changed to P(m,k), since the amount of reception signals changes in accordance with the ratio between P(k,k) and P(m,k), the amount of reception signals will be changed to Sk·{P(m,k)/P(k,k)}". However, actually, when an optical filter being used is switched from the k-th band-pass filter to the m-th band-pass filter, there is a difference in the total amount (total light intensity) of light entering the light receiving section after passing through the respective filters due to the different properties (for example, relative transmittance distribution or relative reflectance distribution) of the respective filters.

As described above, Sk used in Formula (1) above represents all of the reception signals of the light receiving section when the k-th band-pass filter is used. The noise components that are to be calculated are noise components included in all of the reception signals of the light receiving section when the m-th band-pass filter is used. That is, the noise components included in all of the reception signals when the m-th band-pass filter is used are estimated using actual measurement values when the k-th band-pass filter (a filter different from the m-th band-pass filter associated with correction) is used. At that time, there is a difference in the total amount (total light intensity) of light entering the light receiving section after passing through the respective filters due to the different properties (for example, relative transmittance distribution or relative reflectance distribution) of the respective filters. Therefore, by adding signal processing for compensating for the difference in the total light intensity resulting from the different properties of the respective filters when estimating noise, it is possible to further improve the measurement accuracy of the optical spectrum data.

Therefore, in this aspect of the invention, the operational formula of Formula (1) above is multiplied by the correction coefficient R for correcting the difference in the transmittance property or the reflectance property between filters (that is, the operation based on Formula (3) above is executed).

Here, the sum of the transmittance or the reflectance of all of the wavelength bands of the m-th band-pass filter is denoted as ΣQm(1~n), and the sum of the transmittance or the reflectance of all of the wavelength bands of the k-th band-pass filter is denoted as ΣQk(1~n). When the k-th band-pass filter is switched to the m-th band-pass filter, the total amount of light entering the light receiving section will change in accordance with ΣQm(1~n)/ΣQk(1~n). Therefore, all of the reception signals Sk obtained from the light receiving section when the k-th band-pass filter is used will be corrected as Sk·{ΣQm(1~n)/ΣQk(1~n)} when the m-th band-pass filter is used.

The ratio (ΣQm(1~n)/ΣQk(1~n)) of the sum of transmittance properties and reflectance properties between the respective filters will be referred to as the correction coefficient R for correcting (compensating for) the difference in the transmittance properties or the reflectance properties between the respective filters. By multiplying the operational formula of Formula (1) above by the correction coefficient R, the difference in the transmittance properties or the reflectance properties between the respective filters is compensated. Accordingly, the measurement accuracy of the optical spectrum data is improved further.

(8) According to another aspect of the invention, in the spectral measurement device, the optical band-pass filter section is a variable gap etalon filter.

A variable wavelength filter is one type of filter device and is a high-performance optical filter capable of realizing a plurality of filter properties. Since the variable wavelength filter can cover a plurality of wavelength bands using the same filter, it is effective for miniaturization and cost reduction of an optical filter and has excellent usability. Although the variable wavelength filter generally does not have excellent wavelength separation properties, as described above, the measurement accuracy can be improved through correction of the reception data. Therefore, it is possible to realize a spectral measurement device which is small, light, and cheap, and has high measurement accuracy, for example, by using variable wavelength filters having high performance.

(9) According to another aspect of the invention, in the spectral measurement device, the signal processing section measures a spectrophotometric distribution of a measurement target sample based on the reception signal corrected by the correction value.

Through measurement of the spectrophotometric distribution, it is possible to measure the color of a sample and analyze the composition of a sample, for example.

BRIEF DESCRIPTION OF THE DRAWINGS

The invention will be described with reference to the accompanying drawings, wherein like numbers reference like elements.

FIG. 1 is a diagram showing an example of a configuration of a spectral measurement device.

FIGS. 14A and 14B are diagrams illustrating an outline of an estimation method of noise components in a 13-th wavelength band, which are included in the light of a third wavelength band passed through a third band-pass filter.

FIGS. 15A to 15D are diagrams showing a first specific example (correction using Operational Formula (1)) of a method of estimating the amount of the noise components.

FIGS. 16A to 16C are diagrams showing a second specific example (correction using Operational Formula (3)) of a method of estimating the amount of the noise components.

FIGS. 17A to 17C are diagrams illustrating the content of noise removal and correction by a noise removal and correction section.

DESCRIPTION OF EXEMPLARY EMBODIMENTS

Figure 2A:
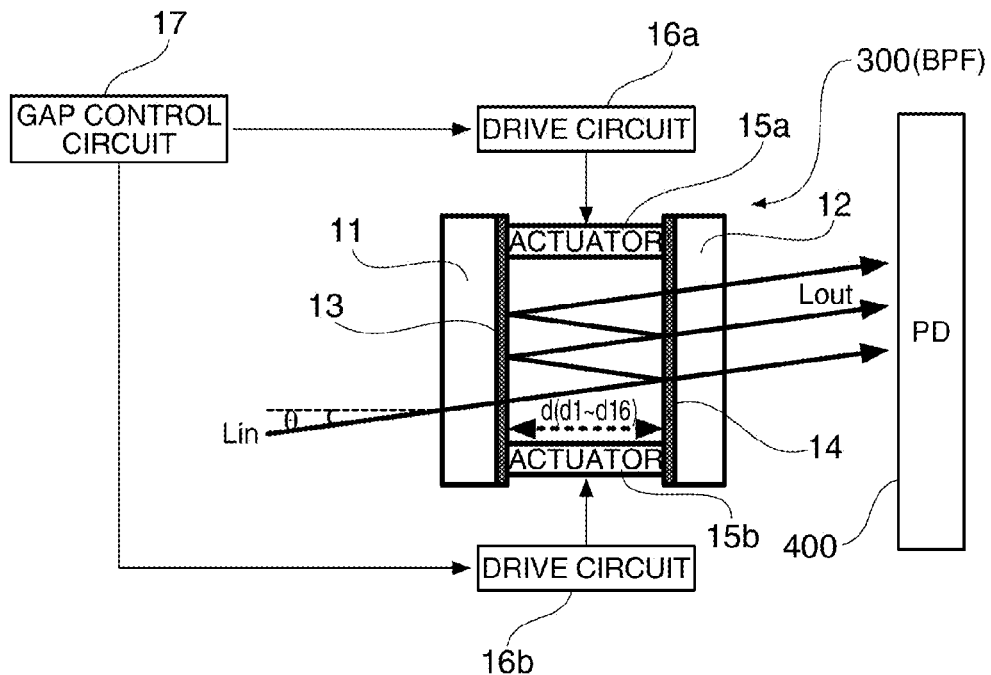
FIGS. 2A and 2B are diagrams showing a configuration example of a variable-gap etalon and an example of band-pass filter properties, respectively.

Hereinafter, embodiments of the invention will be described with reference to the drawings. It should be noted that the embodiments described below do not disadvantageously restrict the content of the invention described in the scope of the claims and not all of the constructions described with reference to the following embodiments are necessary as the solving means of the invention.

First Embodiment

First, an overall configuration of a spectral measurement device (for example, a colorimeter, a spectroscopic analyzer, and an optical spectrum analyzer) will be described.

Example of Overall Configuration of Spectral Measurement Device

FIG. 1 is a diagram showing an example of a configuration of a spectral measurement device. Examples of a spectral measurement device include a colorimeter, a spectroscopic analyzer, and an optical spectrum analyzer. For example, a light source 100 is used when performing color measurement of a sample 200, and a light source 100' is used when performing spectroscopic analysis of the sample 200.

The spectral measurement device includes the light source 100 (or 100'), an optical band-pass filter section (BPF) 300, a light receiving section (PD) 400 using photodiodes and the like, a correction operation section 500 that performs a correction operation (correction processing) for correcting a reception signal (light intensity data) obtained from the light receiving section 400, and a signal processing section 600 that calculates a spectrophotometric distribution and the like based on the light intensity data (reception data) after correction. As the light source 100 (100'), an incandescent bulb, a fluorescent bulb, a discharge tube, alight source (a solid-state lighting source) using a solid-state light emitting element such as an LED, and the like can be used.

The optical band-pass filter section (BPF) 300 functions as a spectrometer and has first to n-th wavelength bands having a predetermined wavelength width as the spectral band thereof (n is an integer of 2 or more, and in the example of FIG. 1, n=16). In the following description, among the first to n-th wavelength bands, an m-th wavelength band ($1 \leq m \leq n$) is sometimes referred to as an interest wavelength band, and a k-th wavelength band ($k \neq m$ and $1 \leq k \leq n$) other than the m-th wavelength band is sometimes referred to as a non-interest wavelength band.

The optical band-pass filter section (BPF) 300 functions as an m-th band-pass filter corresponding to the m-th wavelength band and also functions as a k-th band-pass filter corresponding to the k-th wavelength band. Specifically, the optical band-pass filter section 300 may be a transmission-type optical band-pass filter and may be a reflection-type optical band-pass filter. As the transmission-type optical band-pass filter, a variable-gap etalon filter can be used, for example. As the reflection-type optical band-pass filter, a dichroic mirror (or a dichroic prism), a diffraction grating, and the like can be used, for example. The dichroic mirror is one type of mirror formed of a special optical material, and is an optical filter having a property such that it reflects light of a specific wavelength and transmits light of other wavelengths.

The optical band-pass filter (BPF) 300 of the present embodiment has n spectral bands (n is an integer of 2 or more, and in the example of FIG. 1, n=16), and the wavelength width of the respective spectral bands is set to 20 nm, for example. In FIG. 1, for the sake of convenience, 16 band-pass filters corresponding to the respective 16 spectral bands are illustrated. These 16 band-pass filters are illustrated as the first band-pass filter BPF(1) to the 16th band-pass filter BPF(16). The respective band-pass filters BPF(1) to BPF(16) have a property such that they transmit (or reflect) at least light of a specific wavelength.

The first to 16th optical band-pass filters BPF(1) to BPF(16) corresponding to the respective wavelength bands may be realized using one or plural variable wavelength filters and may be realized by arranging (juxtaposing) 16 fixed wavelength filters having different wavelength bands.

The central wavelengths of the spectral bands associated with the first to 16th band-pass filters BPF(1) to BPF(16) are $\lambda 1$ to $\lambda 16$. For example, the central wavelengths are set such that $\lambda 1=400$ nm, $\lambda 2=420$ nm, $\lambda 3=440$ nm, $\lambda 4=460$ nm, $\lambda 5=480$ nm, $\lambda 6=500$ nm, $\lambda 7=520$ nm, $\lambda 8=540$ nm, $\lambda 9=560$ nm, $\lambda 10=580$ nm, $\lambda 11=600$ nm, $\lambda 12=620$ nm, $\lambda 13=640$ nm, $\lambda 14=660$ nm, $\lambda 15=680$ nm, and $\lambda 16=700$ nm.

The light receiving section (PD) 400 that receives light from the optical band-pass filter section 300 includes 16 photodiodes. That is, these 16 photodiodes are illustrated as the first photodiode PD(1) to the 16th photodiode PD(16). The respective photodiodes PD(1) to PD(16) have reception sensitivity to the above-mentioned respective wavelength bands. When it is possible to use optical sensors having a broad wavelength band to which they have reception sensitivity, one or plural optical sensors may be used.

The correction operation section 500 generates a correction value based on the polarity of a second derivative of the spectral distribution (sometimes referred to as a spectral distribution curve) of a reception signal and corrects the reception signal using the correction value.

As described above, when the curvature (the degree of curvedness) of a spectral distribution curve representing an optical spectrum (a reception light intensity distribution for each wavelength) changes abruptly, particularly, a difference between an integrated value of reception light intensity for each wavelength of the spectral band and an actual reception light intensity at the central wavelength of the spectral band increases. Therefore, the reception signals (reception data) are corrected through signal processing so as to suppress a measurement error (integration error).

The polarity of error is different depending on whether a curve representing the optical spectrum is an upwardly convex curve or a downwardly convex curve. That is, when a reception light intensity value obtained through integration is larger than an actual reception light intensity value, the error has a positive polarity. When the former value is smaller than the latter value, the error has a negative polarity. Thus, it is necessary to change the polarity (positive/negative) of the correction value so as to correspond to the polarity (positive/negative) of the error. Whether the spectral distribution curve is an upwardly convex curve or a downwardly convex curve can be determined by the polarity of a second derivative of the spectral distribution of the reception signal. Therefore, the correction operation section 500 generates the correction value based on the polarity of the second derivative of the spectral distribution of the reception signal and corrects the reception signal (reception data, reception light intensity data) using the correction value. As described above, this correction is sometimes referred to as integration error correction.

For example, by superimposing the correction value on the reception signal, namely by adding the correction value to the reception signal or subtracting the correction value from the reception signal, it is possible to correct the reception signal. Moreover, the reception signal can also be corrected by multiplying the reception signal by the correction value (correction coefficient). The measurement error is reduced by the correction operation. Therefore, it is possible to perform high-accuracy spectral measurement, for example, by using an optical filter (variable wavelength filter and the like) which has good usability and is relatively cheap and small.

The correction operation section 500 can execute base floating correction in addition to the integration error correction. An example of executing the base floating correction together will be described in the second embodiment.

Specific Example of Configuration of Optical Band-Pass Filter Section

Figure 2B:
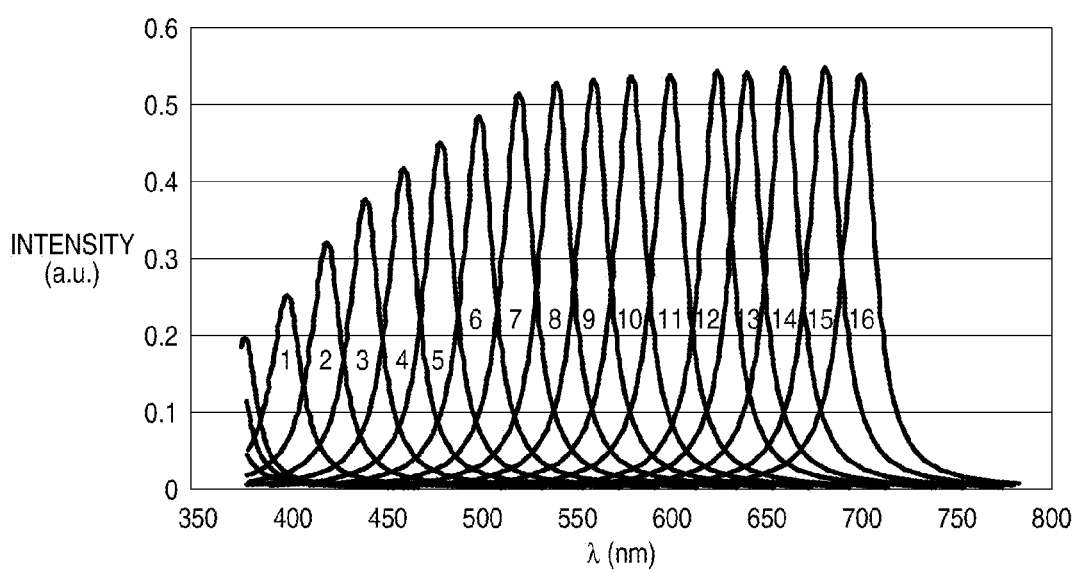

FIGS. 2A and 2B are diagrams showing a configuration example of a variable-gap etalon and an example of band-pass filter properties, respectively. As shown in FIG. 2A, a variable-gap etalon filter includes a first substrate 11 and a second substrate 12 disposed to face each other, a first reflection film 13 formed on the principal surface (front surface) of the first substrate 11, a second reflection film 14 formed on the principal surface (front surface) of the second substrate 12, and a first actuator (for example, a piezoelectric element or the like) 15a and a second actuator 15b which are interposed between the respective substrates so as to adjust a gap (distance) between the respective substrates.

The first and second actuators 15a and 15b are driven by a first drive circuit 16a and a second drive circuit 16b, respectively. Moreover, the operation of the first and second drive circuits 16a and 16b is controlled by a gap control circuit 17.

Light Lin incident from the outside at a predetermined angle θ passes through the first reflection film 13 substantially being seldom scattered. The reflection of light occurs repeatedly between the first reflection film 13 formed on the first substrate 11 and the second reflection film 14 formed on the second substrate 12. In this way, interference of light occurs, part of the incident light passes through the second reflection film 14 on the second substrate 12, and output light Lout reaches the light receiving section 400 (the photodiode PD). Which wavelength of light will be strengthened by the interference depends on the gap d between the first substrate 11 and the second substrate 12. Therefore, it is possible to change the wavelength band (spectral band) of light passing through the second reflection film 14 by controlling the gap d variably. For example, 16 spectral bands can be realized by controlling the gap d so as to be changed from d1 to d16.

FIG. 2B shows a spectral property of the variable-gap etalon filter (specifically, a relative spectral intensity for each of 16 wavelength bands each having a width of 20 nm). When a variable-gap etalon filter is used as the optical band-pass filter section (optical filter section) 300, since a plurality of transmission wavelength bands can be realized using one filter, it is possible to obtain a spectrometer section which is simple, small, and cheap.

Figure 3:
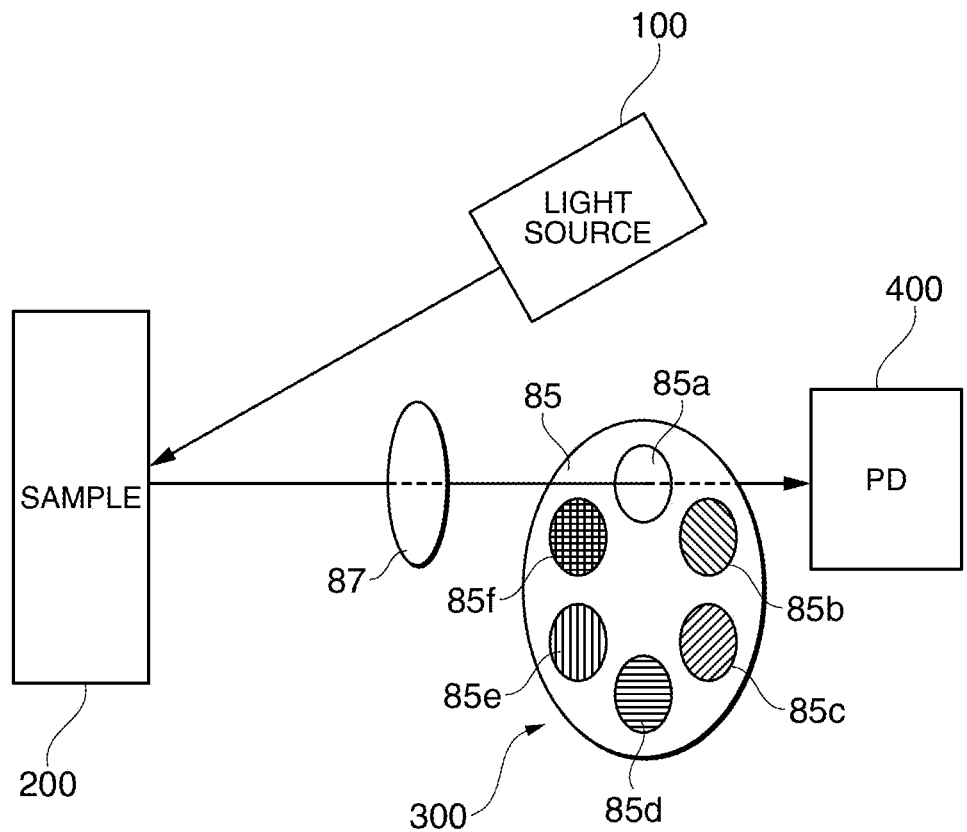
FIG. 3 is a diagram showing an example of a configuration of a rotary band-pass filter used as an optical band-pass filter.

FIG. 3 is a diagram showing an example of a configuration of a rotary band-pass filter used as an optical band-pass filter. A rotary band-pass filter includes an optical system (lens) 87 and a rotatable disk 85 in which a plurality of band-pass filters 85a to 85f having different transmission wavelength bands is incorporated. One of the band-pass filters 85a to 85f is selected in accordance with a measurement target wavelength band and measurement is executed.

Figure 4:
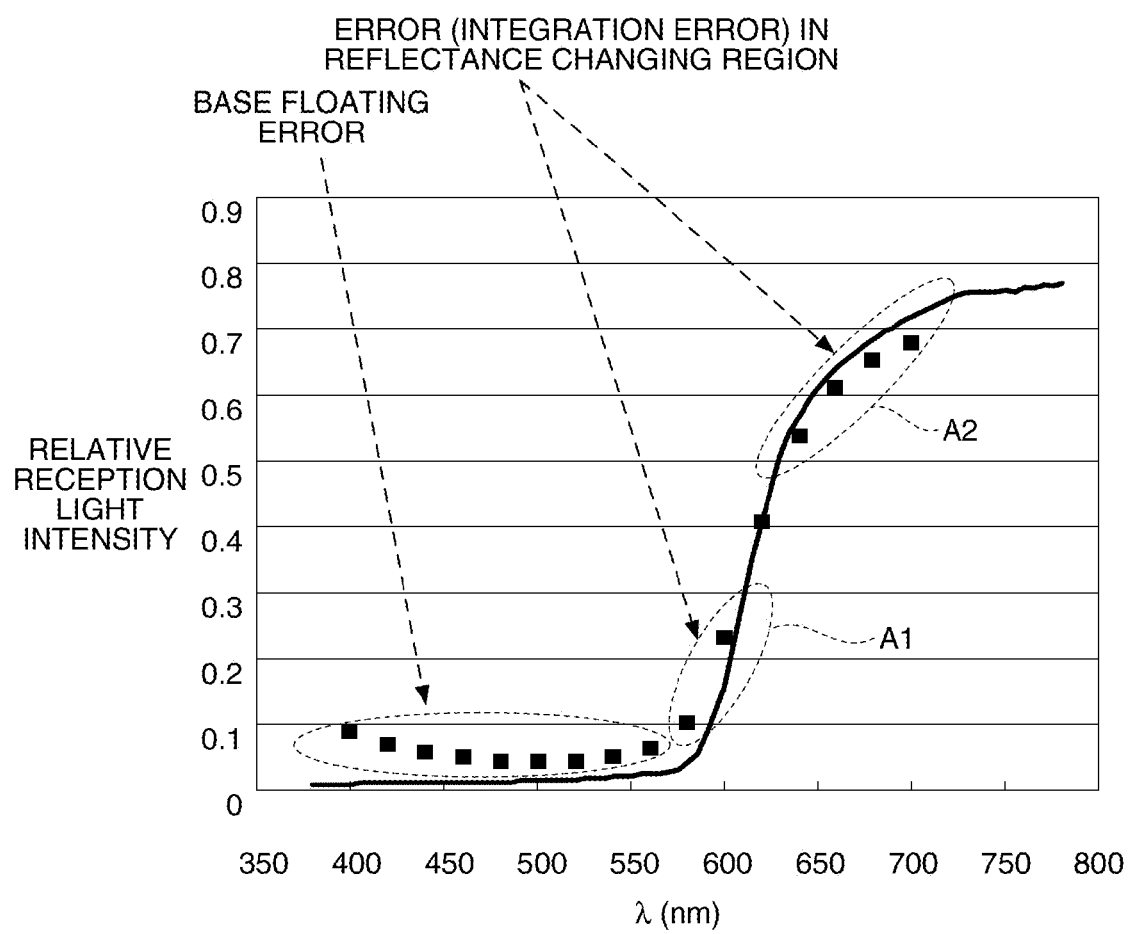
FIG. 4 is a diagram showing, for the purpose of comparison, a spectral distribution curve (in this example, spectral reflectance distribution curve) generated based on 16-point data before correction, actually measured by the spectral measurement device of FIG. 1 and an actual spectral distribution (spectral reflectance distribution) of a sample.

FIG. 4 is a diagram showing, for the purpose of comparison, a spectral distribution curve (in this example, spectral reflectance distribution curve) generated based on 16-point data before correction, actually measured by the spectral measurement device of FIG. 1 and an actual spectral distribution (spectral reflectance distribution) of a sample. The spectral reflectance distribution curve is generated, for example, by the following procedure. The surface color of a sample being used is red. The spectral measurement device shown in FIG. 1 is used as a colorimeter (color measurement device), and light reflected from a sample is received by the light receiving section 400 to obtain reception data of 16 points. Then, a spectral reflectance distribution curve is generated based on the reception data. In FIG. 4, the horizontal axis represents a wavelength, and the vertical axis represents a relative reception light intensity. Moreover, the 16-point data before correction are indicated by black squares, and the actual spectral distribution (spectral reflectance distribution) of the sample is indicated by a solid line.

In the example of FIG. 4, a phenomenon (so-called base floating) in which the actual measurement value in the wavelength band of 400 nm to 560 nm is higher than the actual reception light intensity occurs. Moreover, in the wavelength band of 580 nm to 700 nm, an error (integration error) resulting from a change in the spectral reflectance of the sample 200 occurs.

Regarding the error (integration error) resulting from the change in the spectral reflectance of the sample 200, two kinds of phenomena occur. The first is a phenomenon in which the actual measurement value is higher than the actual reception light intensity in a wavelength band (wavelength band A1) corresponding to the wavelengths 580 nm and 600 nm. The second is a phenomenon in which the actual measurement value is lower than the actual reception light intensity conversely in a wavelength band (wavelength band A2) of 640 nm to 700 nm. Moreover, the actual measurement data in the wavelength of 620 nm corresponds to an inflection point (a point where the second derivative is zero) of the spectral distribution curve, and thus, substantially no error occurs.

In the present embodiment, the error (integration error) resulting from the change in the spectral reflectance of the sample in the wavelength bands A1 and A2 is corrected using the correction value, thus making it possible to generate more accurate spectral reflectance. This will be described in detail below.

Figure 5A:
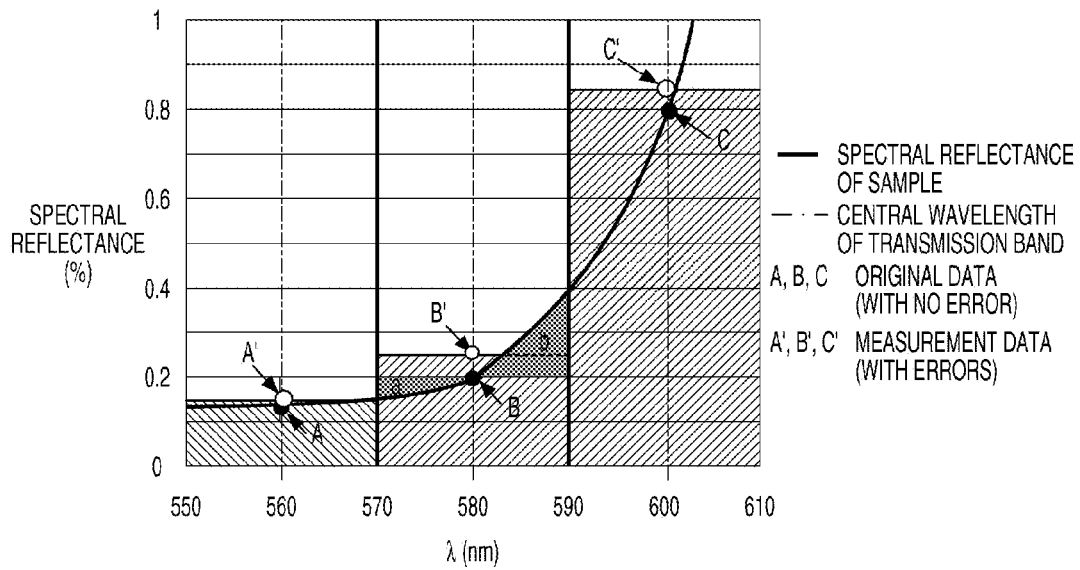
FIGS. 5A and 5B are diagrams illustrating the cause of an error (integration error) resulting from a change in the spectral reflectance of a sample.
Figure 5B:
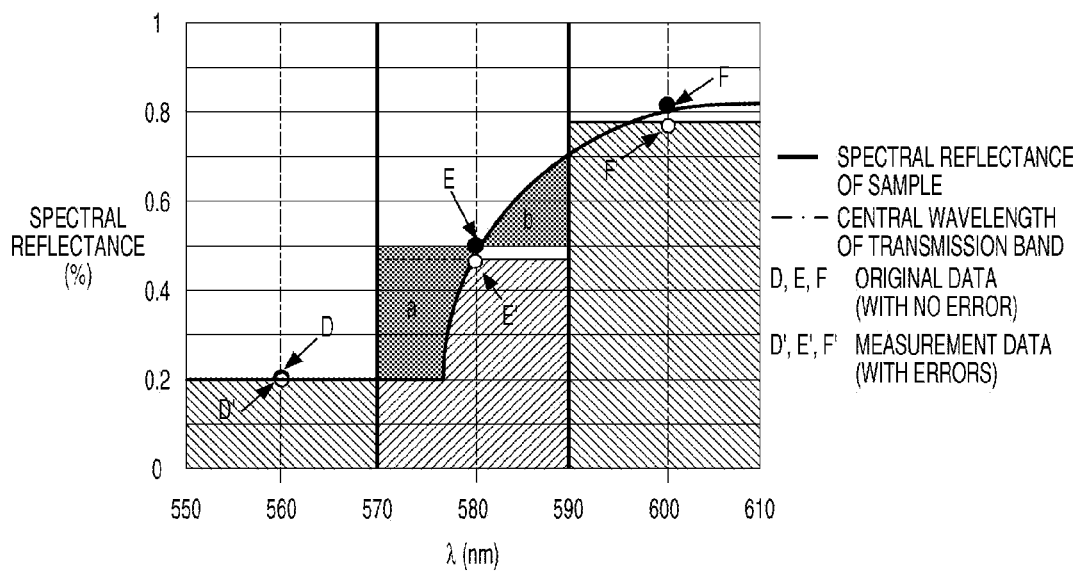

Cause of Error (Integration Error) Resulting from Change in Spectral Reflectance of Sample FIGS. 5A and 5B are diagrams illustrating the cause of an error (integration error) resulting from a change in the spectral reflectance of a sample. The spectral distribution curve shown in FIG. 5A is a curve (downwardly convex curve) in which the second derivative is positive. The spectral distribution curve shown in FIG. 5B is a curve (upwardly convex curve) in which the second derivative is negative.

In FIG. 5A, a bold solid line represents a spectral reflectance curve representing the actual spectral reflectance of the sample 200. This spectral reflectance curve is a downwardly convex curve (second derivative: positive). Moreover, the points A, B, and C indicated by black circles represent reception light intensities (ideal reception light intensities) with no error at the respective central wavelengths (560 nm, 580 nm, and 600 nm) of three spectral wavelength bands (550 nm, to 570 nm, 570 nm, to 590 nm, and 590 nm to 610 nm) having a width of 20 nm. Furthermore, the points A', B', and C' represent the actual measurement values with errors (namely, the integrated values of the reception light intensities in the respective wavelength bands having the width of 20 nm). In FIG. 5A, the integrated values (smoothed areas) of the respective wavelength bands are indicated by hatching.

Here, a wavelength band of 570 nm to 590 nm will be focused on, for example. The reception light intensity of this spectral wavelength band can be obtained by integrating (smoothing) the reception light intensities (spectral intensities) corresponding to the respective wavelengths of 570 nm to 590 nm. The integrated value of the reception light intensities will be used as a reception light intensity corresponding to the central wavelength 580 nm of this spectral wavelength band. Here, regions a and b will be focused on.

If the areas of the regions a and b are the same, a reception light intensity level B' after integration (smoothing) is identical to an ideal reception light intensity B. However, in FIG. 5A, since the curve (spectral distribution curve) representing the spectral distribution of the wavelength band of 570 nm to 590 nm is a downwardly convex curve, and the curvature of the spectral distribution curve changes abruptly, the area of the region a is larger than the area of the region b. Thus, an error corresponding to the difference in the area occurs, and the level B' of the integrated value is higher than the ideal reception light intensity B. In this way, an integration error (an error resulting from the change in the spectral reflectance of the sample) occurs.

In the vicinity of the point A where the change in the spectral reflectance of the sample 200 is small, there is substantially no difference in the levels of the points A and A' (since the areas of the regions a and b are substantially the same). In contrast, in the vicinity of the point B where the change in the spectral reflectance of the sample 200 is large, there is a difference in the areas of the regions a and b (the effect of a<b becomes obvious), and accordingly, the level of the point B' is higher than the level of the point B. Similarly, in the vicinity of the point C, the level of the point C' is higher than the level of the point C.

On the other hand, in FIG. 5B, the spectral distribution curve representing the spectral reflectance of the sample 200 is illustrated as a curve (upwardly convex curve) in which the second derivative is negative. The points D, E, and F represent the ideal reception light intensities at the central wavelengths of the respective wavelength bands. Moreover, the points D', E', and F' represent the actual measurement values with errors.

In the example of FIG. 5B, a wavelength band of 570 nm to 590 nm will be focused on. Regarding the respective areas of the regions a and b in this wavelength band, a relation of a>b is satisfied. Therefore, an error corresponding to the difference between the areas occurs, and the level E' of the actual integrated value is lower than the ideal reception light intensity E. In this way, an integration error (an error resulting from the change in the spectral reflectance of the sample) occurs.

In the vicinity of the point D where the change in the spectral reflectance of the sample 200 is small, there is substantially no difference in the levels of the points D and D' (since the areas of the regions a and b are substantially the same). On the other hand, in the vicinity of the point E where the change in the spectral reflectance of the sample 200 is large, the level of the point E' is lower than the level of the point E. Similarly, the level of the point F' is lower than the level of the point F.

As described above, whether the level of the actual measurement value will be higher or lower than the ideal level depends on the shape of the spectral distribution curve (that is, whether the second derivative of the spectral distribution curve is positive or negative). Therefore, when calculating the correction value, it is preferable to change the polarity (positive/negative) of the correction value so as to correspond to the polarity (positive/negative) of the second derivative of the spectral distribution curve. Moreover, since the degree of error (the amount of error) increases when the spectral distribution changes abruptly, it is preferable to change the magnitude of the correction value variably in accordance with the degree of the change in the spectral distribution to execute correction on a case by case basis.

Figure 6:
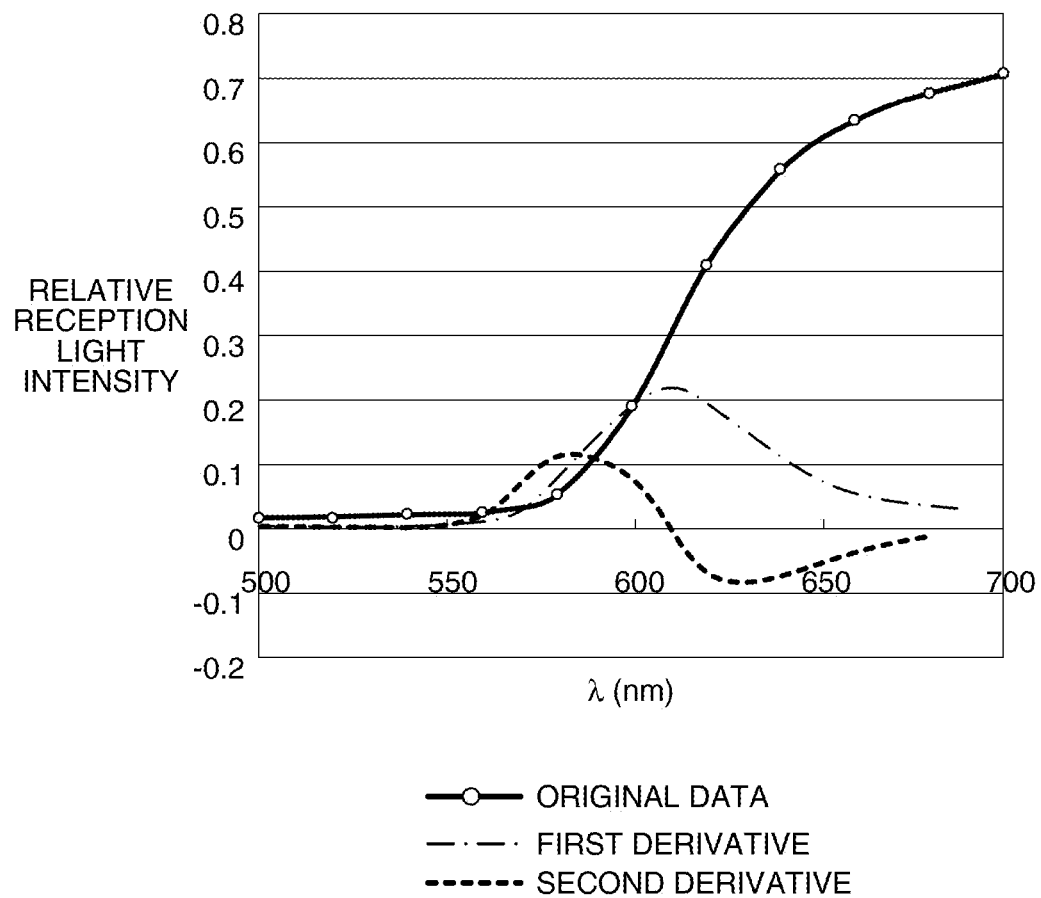
FIG. 6 is a diagram showing a change in the first and second derivatives of a spectral distribution curve obtained through computer simulation.

FIG. 6 is a diagram showing a change in the first and second derivatives of a spectral distribution curve obtained through computer simulation. In FIG. 6, the solid line represents the spectral distribution curve (spectral reception light intensity curve) representing the spectral reflectance of the sample 200, the one-dot chain line represents the change in the first derivative, and the bold dotted line represents the change in the second derivative. As shown in the drawing, the second derivative changes abruptly in the wavelength band of 570 nm to 590 nm. Therefore, as described in FIG. 5A, the integration error (an error resulting from the change in the spectral reflectance of the sample) becomes most obvious in the wavelength band of 570 nm to 590 nm.

Figure 7A:
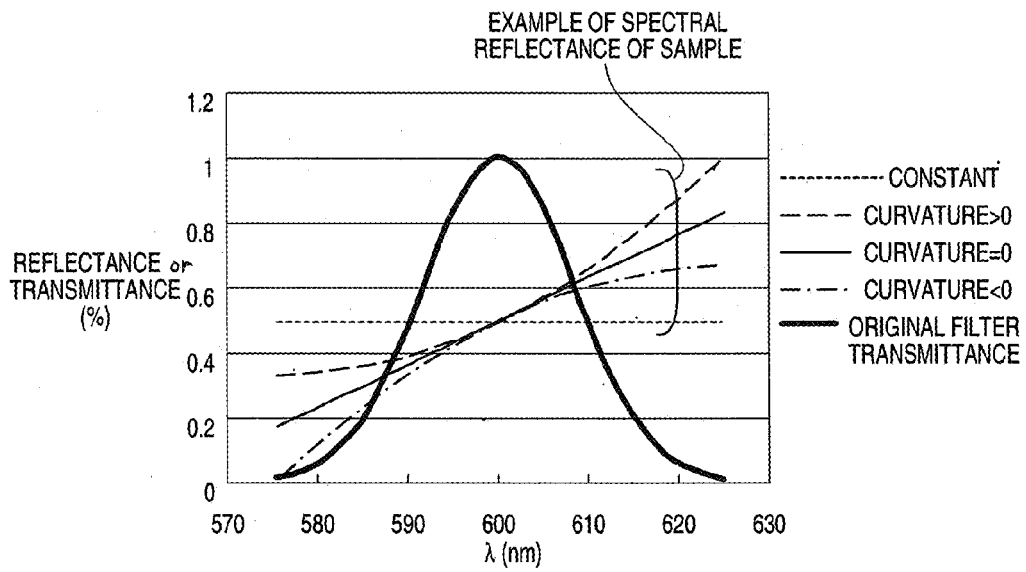
FIGS. 7A and 7B are diagrams showing examination results based on computer simulation on how a reception light intensity distribution (spectral light intensity distribution) obtained by a photodiode receiving light having passed through an optical band-pass filter will change in accordance with the shape of a characteristic line representing a spectral reflectance of a sample.
Figure 7B:
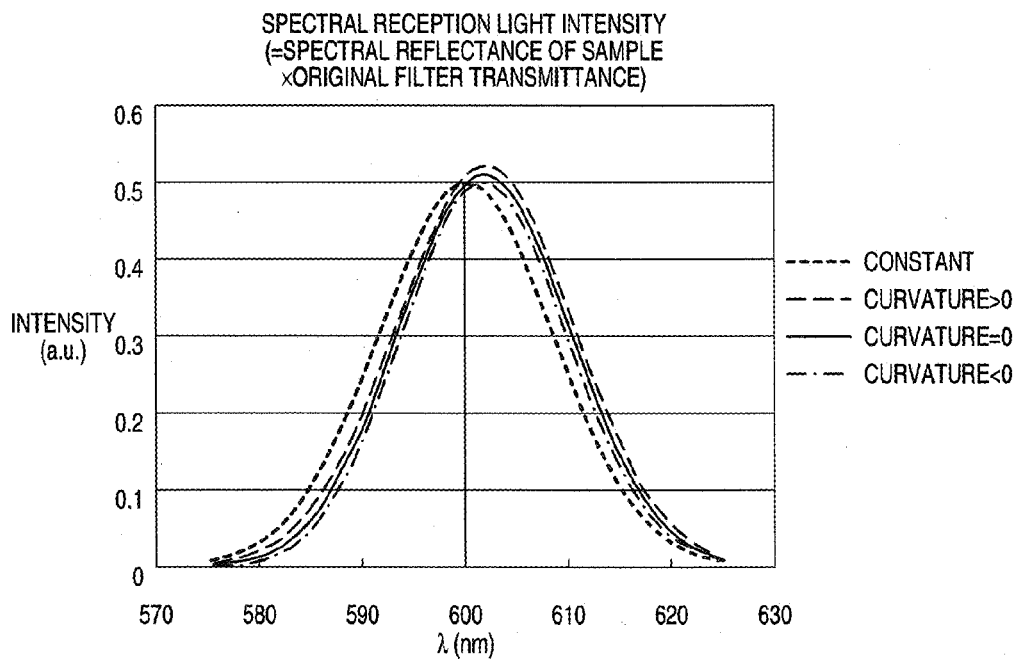

FIGS. 7A and 7B are diagrams showing examination results based on computer simulation on how a reception light intensity distribution (spectral light intensity distribution) obtained by a photodiode receiving light having passed through an optical band-pass filter will change in accordance with the shape of a characteristic line representing a spectral reflectance of a sample.

In FIG. 7A, the spectral property (spectral transmittance property) of the optical band-pass filter is indicated by a bold solid line. In this computer simulation, characteristic lines representing the spectral reflectance of four samples are used. One is a spectral reflectance curve (curvature>0: a downwardly convex curve) indicated by a sparsely dotted line; another is a spectral reflectance curve (curvature=0: a monotonically increasing straight line) indicated by a solid line; yet another is a spectral reflectance curve (curvature<0: an upwardly convex curve) indicated by one-dot chain line; and still another is a straight line (a straight line having an inclination of 0) having a constant spectral reflectance indicated by a fine dotted line.

FIG. 7B shows the reception light intensity distributions (spectral light intensity distributions) corresponding to the respective samples. The spectral reception light intensity obtained by the photodiode receiving light having passed through the optical band-pass filter can be calculated by multiplying the spectral reflectance of the sample by the spectral transmittance of the optical band-pass filter.

In FIG. 7B, the spectral reception light intensity property indicated by a dotted line corresponds to the sample in which the spectral reflectance is constant. The shape of the curve representing the spectral reception light intensity property indicated by the dotted line is identical to the shape of the spectral transmittance curve of the optical band-pass filter.

In contrast, in the curves representing the spectral reception light intensity properties corresponding to the other three samples, since the spectral reflectance of the samples increases towards the high-wavelength band, the curves representing the spectral reception light intensity properties also shift towards the high-wavelength band (right side). Here, the sparsely dotted curve corresponds to the sample indicated by the curve having the positive curvature (>0); the solid line corresponds to the sample in which the spectral reception light intensity is indicated by a monotonically increasing straight line; and the one-dot chain line corresponds to the sample indicated by the curve having the negative curvature (<0).

However, the spectral light intensity distribution corresponding to the sample having the positive curvature (>0) has a higher level in the respective wavelength bands than the spectral light intensity distribution corresponding to the sample having the zero curvature (=0). Moreover, the spectral light intensity distribution corresponding to the sample having the negative curvature (<0) has a lower level in the respective wavelength bands than the spectral light intensity distribution corresponding to the sample having the zero curvature (=0).

As described above, when the spectral reflectance of the sample is represented by a curve, the following is made clear through computer simulation. That is, when the curvature of the spectral reflectance curve is larger than 0 (a downwardly convex curve), the actual measurement value shifts towards a high-level side. On the other hand, when the curvature of the spectral reflectance curve is smaller than 0 (an upwardly convex curve), the actual measurement value shifts towards a low-level side. This result proves the phenomenon described earlier using FIGS. 5A and 5B.

In the present embodiment, based on such discussion, the correction operation section 500 (FIG. 1) generates a correction value based on the polarity of the second derivative of the spectral distribution (spectral distribution curve) of the reception signal and corrects the reception signal using the correction value.

Specifically, for example, when the second derivative is positive (the curvature of the curve representing the spectral reception light intensity is larger than 0), the correction operation section 500 decreases the value of the reception signal (reception data) through correction using the correction value. When the second derivative is negative (the curvature of the curve representing the spectral reception light intensity is smaller than 0), the correction operation section 500 increases the value of the reception signal (reception data) through correction using the correction value. In order to perform such correction, the spectral measurement device of the present embodiment is provided with the correction operation section 500 having a configuration as shown in FIG. 8.

Specific Configuration Example of Spectral Measurement Device

Figure 8:
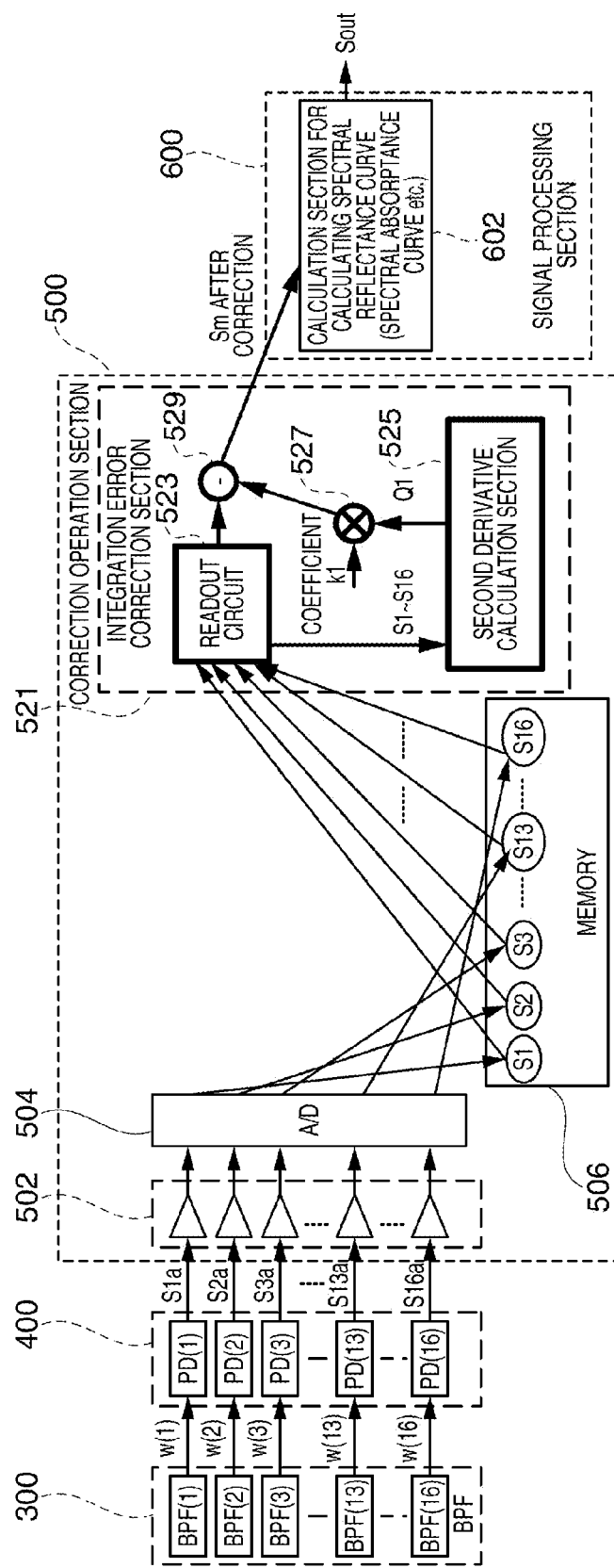
FIG. 8 is a diagram illustrating a configuration example of a correction operation section provided in the spectral measurement device and an outline of a correction operation.

FIG. 8 is a diagram illustrating a configuration example of a correction operation section provided in the spectral measurement device and an outline of a correction operation.

In FIG. 8, dispersed light components w(1) to w(16) are output from the first to 16th band-pass filters BPF(1) to BPF (16) included in the optical band-pass filter section 300. The first to 16th photodiodes PD(1) to PD(16) included in the light receiving section 400 receive the dispersed light components w(1) to w(16) and output electric signals (analog reception signals) S1a to S16a (the ending characteristics a indicate that they are analog signals) corresponding to reception light intensities through photoelectric conversion.

The correction operation section 500 includes, for example, an initial-stage amplifier 502 that amplifies the reception signal output from the light receiving section 400, an A/D converter 504 that converts the output signal (analog signal) of the initial-stage amplifier 502 into a digital signal, a memory 506 that can be used for storing various types of data, and an integration error correction section 521.

The integration error correction section 521 includes a readout circuit 523 that reads out the reception data from the memory 506, a second derivative calculation section 525 that calculates a second derivative of a spectral light intensity distribution (a broad-sense spectral distribution or a spectral distribution curve) based on the reception data, a multiplication section 527 of a correction coefficient (k1: a real number), and a correction value superimposition section (correction value addition/subtraction section) 529 that superimposes (adds or subtracts) the correction value output from the multiplication section 527 on the readout reception data (reception signal).

The memory 506 temporarily stores the reception data (or reception light intensity data) S1 to S16 output from the A/D converter 504.

The readout circuit 523 reads out the reception data S1 to S16 from the memory 506. The second derivative calculation section 525 calculates the second derivative Q1 of the spectral distribution (spectral distribution curve) based on the readout reception data S1 to S16. A calculation method will be described later with reference to FIGS. 9A to 9C.

The correction coefficient multiplication section 527 multiplies the calculated second derivative Q1 by a correction coefficient k1. The correction coefficient k1 may be a fixed value and may be adaptively generated on a case by case basis. A correction value Cx for a correction target spectral band is calculated through an operation based on the second derivative and the correction coefficient k1.

As described above, when the polarity of the second derivative Q1 is positive, the spectral distribution curve is a downwardly convex curve. When the polarity of the second derivative Q1 is negative, the spectral distribution curve is a upwardly convex curve. Moreover, when the curvature of the spectral distribution curve increases (the spectral intensity changes abruptly), the absolute value of the second derivative Q1 increases. That is, the second derivative Q1 (positive or negative) serves as information on the shape of the spectral distribution curve (information on whether the curve is upwardly convex or downwardly convex) and information on the abruptness of the change in the spectral distribution (information on whether or not the change is abrupt or smooth).

Focusing on this property, in the present embodiment, the second derivative Q1 is used as the basic data for calculation of the correction value. That is, as described above, the correction value Cx for a correction target spectral band is calculated through an operation (specifically, multiplication of the second derivative Q1 by the correction coefficient k1) based on the calculated second derivative Q1 and the correction coefficient k1 (k1 is a real number). The correction value Cx has a property such that it has a polarity (positive/negative) corresponding to the upward/downward convex shape of the spectral distribution curve and the magnitude of the absolute value thereof increases in proportion to the abruptness of the change in the spectral distribution curve. Therefore, the correction value Cx which has an appropriate value corresponding to the shape of the spectral distribution curve and the abruptness thereof is obtained by a simple method.

If k1=1, the second derivative Q1 is used as the correction value as it is. Moreover, although the correction coefficient k1 is basically a positive real number excluding 0, k1 may exceptionally be set to 0 (for example, when no correction is executed). According to this method, the correction value of which the magnitude is variably controlled can be generated quickly (for example, real-time) by a simple method (simple configuration).

In the correction value superimposition section 529, the correction value Cx output from the multiplication section 527 is superimposed (added or subtracted) on the reception data (reception signal) read out by the readout circuit 523 (specifically, the correction value Cx is subtracted from the reception data (reception signal), for example). In this way, the integration error correction is executed, and the reception data (reception signal) Sm (m=1 to 16) having been subjected to integration error correction are obtained.

The signal processing section 600 includes a calculation section 602 for calculating a spectral reflectance curve or a spectral absorptance curve. The signal processing section 600 executes predetermined signal processing based on the corrected reception signal (corrected reception data) corrected by the correction operation section 500 to calculate a spectrophotometric distribution, for example. The signal processing section 600 outputs a signal (that is, spectrophotometric distribution information) Sout representing the calculated spectral intensities for each wavelength.

The example above is just an example, and other correction methods may be used. In the example above, although the reception data are corrected by superimposing (adding or subtracting) the correction value on the reception data, the reception data may be corrected by multiplying the reception data by the correction value (correction coefficient). Moreover, a predetermined fixed value may be used as the correction value, and a correction value (variable correction value) of which the value changes in accordance with the degree of the change in the spectral distribution curve may be used. Furthermore, when a variable correction value is used, a method in which the value of the correction value is continuously changed in accordance with the degree of the change in the spectral distribution may be used. Alternatively, a method in which the degree of the change in the spectral distribution may be divided into a plurality of steps using a threshold or the like, and the value of the correction value is changed (switched) gradually in accordance with the respective steps may be used.

Figure 9A:
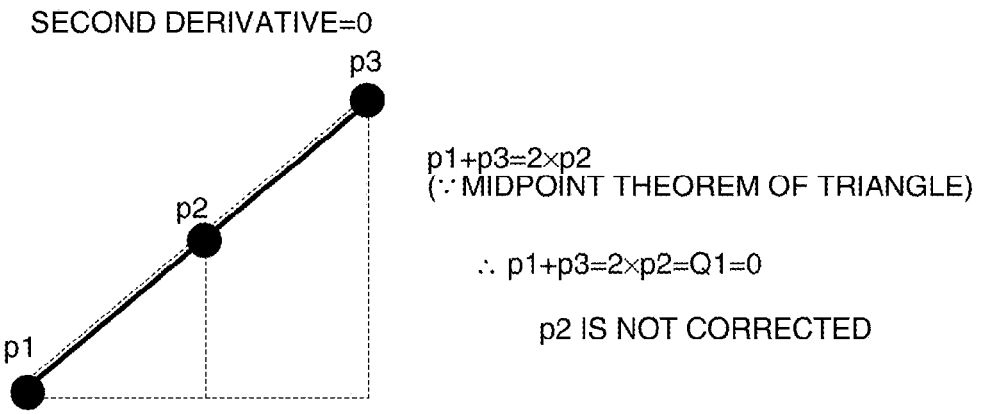
FIGS. 9A to 9C are diagrams illustrating examples of a calculation method of a second derivative.
Figure 9B:
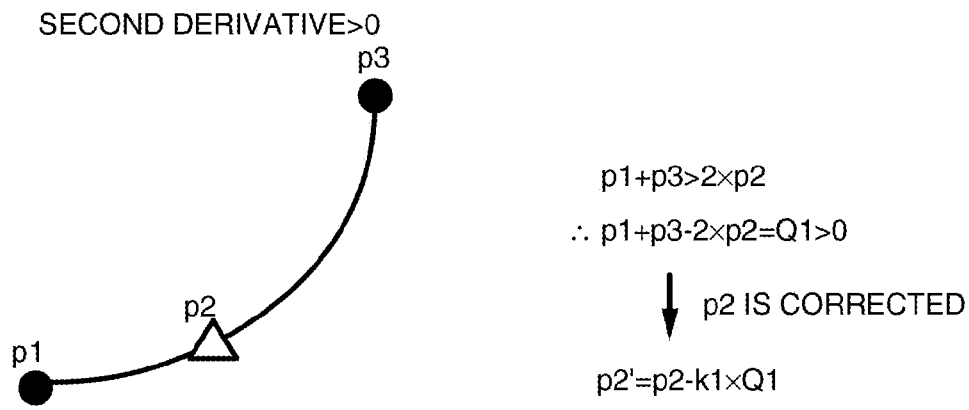
Figure 9C:
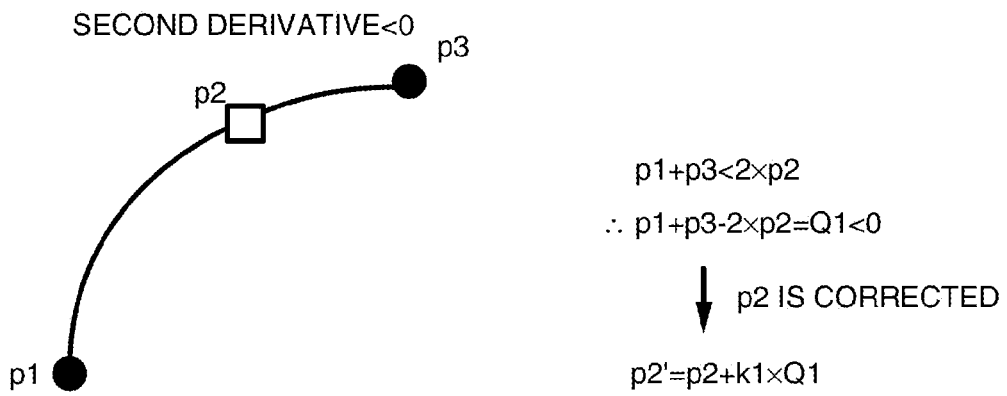

Next, an example of a calculation method of the second derivative will be described. FIGS. 9A to 9C are diagrams illustrating examples of a calculation method of the second derivative. In the examples shown in FIGS. 9A to 9C, when the reception light intensity of the first spectral band is p1, the reception light intensity of the second spectral band adjacent to the first spectral band is p2, and the reception light intensity of the third spectral band adjacent to the second spectral band is p3, the second derivative Q1 is calculated by an operation based on $Q1=(p1+P3-2\cdot p2)$.

FIG. 9A shows an example where the second derivative is 0, FIG. 9B shows an example where the second derivative is positive (>0), and FIG. 9C shows an example where the second derivative is negative (<0).

In the example of FIG. 9A, the spectral distribution changes (increases) in a straight line. When the reception light intensity of the first spectral band is p1, the reception light intensity of the second spectral band adjacent to the first spectral band is p2, and the reception light intensity of the third spectral band adjacent to the second spectral band is p3, a relation of $p1+P3=2\cdot p2$ is satisfied by the midpoint theorem of a triangle (indicated by dotted lines). The second derivative Q1 can be calculated by an operation of $Q1=p1+P3-2\cdot p2$. In the example of FIG. 9A, Q1=0 (the second derivative is zero). In this case, since no integration error occurs, the integration error correction is not necessary.

In the example of FIG. 9B, a relation of $Q1=p1+p3-2\cdot p2>0$ is satisfied. That is, when the spectral distribution curve is downwardly convex, the second derivative Q1 is positive. As described earlier, when the spectral distribution curve is downwardly convex, the actual measurement value tends to be larger than an actual value (ideal value). Therefore, in the example of FIG. 9B, the reception light intensity p2 of the second spectral band (correction target spectral band) is corrected using a correction value ($=k1\cdot Q1$). That is, the integration error correction section 521 of the correction operation section 500 executes a correction operation of $p2'=p2-k1\cdot Q1$ to calculate corrected reception light intensity data p2' for the second spectral band.

In the example of FIG. 9C, a relation of $Q1=p1+p3-2\cdot p2<0$ is satisfied. That is, when the spectral distribution curve is upwardly convex, the second derivative Q1 is negative. When the spectral distribution curve is upwardly convex, the actual measurement value tends to be smaller than an actual value (ideal value). Therefore, in the example of FIG. 9C, the reception light intensity p2 of the second spectral band (correction target spectral band) is corrected using a correction value ($=k1\cdot Q1$). That is, the integration error correction section 521 of the correction operation section 500 executes a correction operation of p2'=p2+k1·Q1 to calculate corrected reception light intensity data p2' for the second spectral band.

The example above is just an example, and the second derivative may be calculated by other methods. In the example above, the second derivative is calculated by a simple operation which uses the measurement data of three adjacent wavelength bands. However, in order to detect the change in the curvature of the spectral distribution curve more accurately, a method in which a plane curve (approximated curve) is estimated based on the actual measurement values (discrete values), and the second derivative of the plane curve is calculated may be used.

Figure 10:
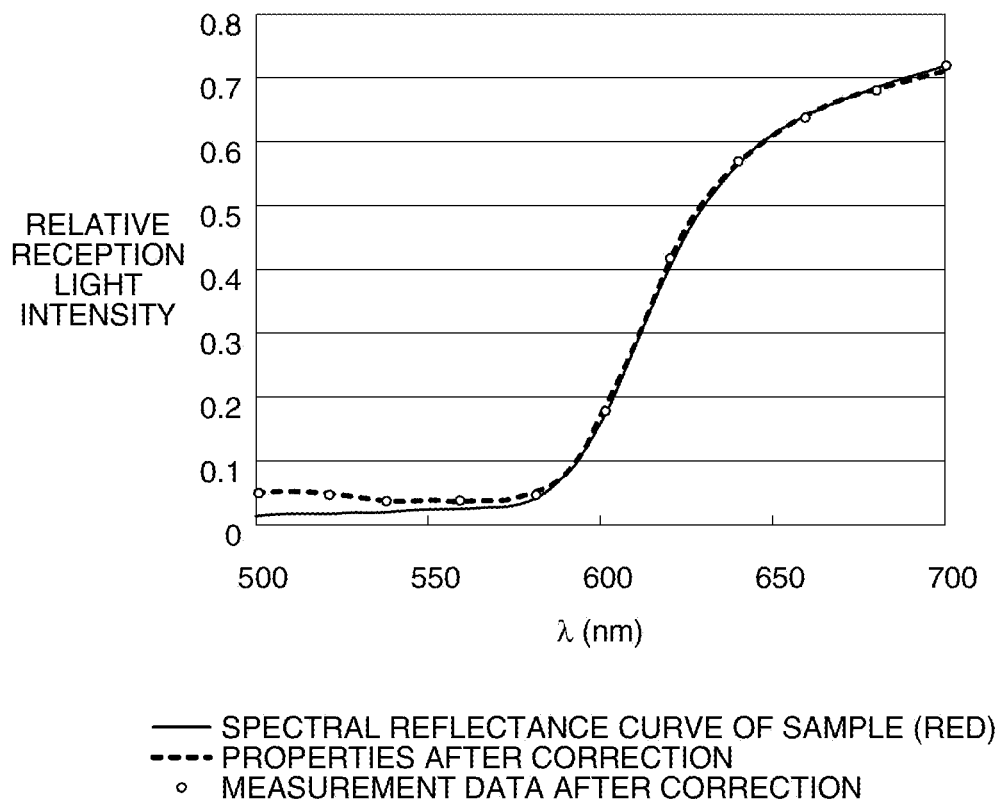
FIG. 10 is a diagram showing, for the purpose of comparison, a spectral distribution curve (in this example, a spectral reflectance distribution curve) generated based on 16-point data after integration error correction and an actual spectral distribution (in this example, a spectral reflectance distribution) of a sample.

FIG. 10 is a diagram showing, for the purpose of comparison, a spectral distribution curve (in this example, a spectral reflectance distribution curve) generated based on 16-point data after integration error correction and an actual spectral distribution (in this example, a spectral reflectance distribution) of a sample. The spectral reflectance distribution curve is generated, for example, by the following procedure. The surface color of a sample being used is red. The spectral measurement device shown in FIG. 1 is used as a colorimeter (color measurement device), and light reflected from a sample is received by the light receiving section 400 to obtain reception data of 16 points. Then, the above-described integration error correction is executed on the reception data, and a spectral reflectance distribution curve is generated based on the reception signal (reception data) after correction. In FIG. 10, the spectral reflectance values based on the measurement data (16-point data) after correction are indicated by white circles. Moreover, the corrected spectral property based on the corrected measurement data is indicated by a dotted line.

As will be clear from FIG. 10, the spectral reflectance value based on the actual measurement data in a wavelength band in the vicinity of the wavelengths 580 nm to 700 nm (a wavelength region where the spectral reflectance of the sample changes) is substantially identical to the actual spectral reflectance value of the sample. Here, the spectral property after correction shown in FIG. 10 is compared with the spectral property before correction shown in FIG. 4. From the comparison, it can be understood that in the spectral property after correction shown in FIG. 10, the error (integration error) in the spectral reflectance changing region is sufficiently suppressed.

Second Embodiment

In the spectral property after correction shown in FIG. 10, a base floating error remains in the wavelength band of 400 nm to 560 nm. If it is possible to reduce the base floating error, it is possible to further improve the measurement accuracy of the spectral measurement device. Therefore, in the present embodiment, base floating error correction is executed in addition to the integration error correction.

The base floating error occurs, for example, when the half bandwidth of the optical band-pass filter 300 is broad (the wavelength separation property is not high). That is, although an optical band-pass filter associated with a desired wavelength band ideally transmits only light of the wavelength band, light of wavelengths other than the desired wavelength band is also mixed into the transmission light. Therefore, a noise component (reception component corresponding to wavelengths other than the desired wavelength band) is superimposed on the reception signals of the respective wavelength bands, and the reception signal level increases by an amount corresponding to the noise component. Thus, a base floating error occurs.

Therefore, in the present embodiment, a correction operation (base floating correction) is executed in which the sum of the noise component for each wavelength band included in all of the reception signals (that is, interest reception signals) obtained by receiving light from the m-th band-pass filter, and the calculated sum of noise components is subtracted from all of the reception signals to thereby suppress the effect of noise. This base floating correction is preferably executed prior to the integration error correction. That is, noise is removed from the spectroscopic data of the respective spectral bands (spectral wavelength bands) through the base floating correction, and the integration error correction is executed based on the spectroscopic data in which the noise is removed. Thus, correction accuracy can be further improved.

Configuration Example of Correction Operation Section

Figure 11:
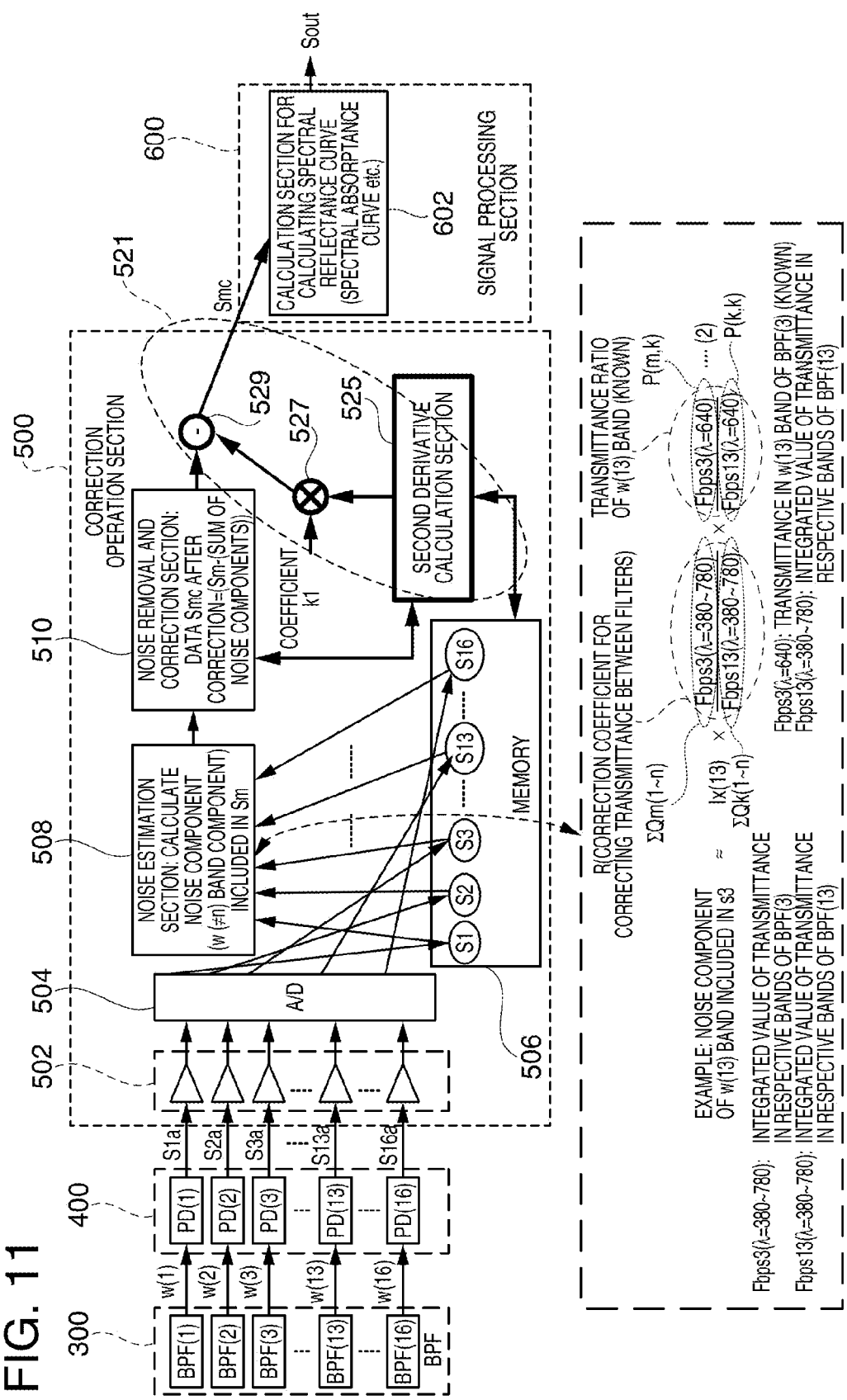
FIG. 11 is a diagram illustrating a configuration example of a correction operation section and an outline of a correction operation according to a second embodiment.

FIG. 11 is a diagram illustrating a configuration example of a correction operation section and an outline of a correction operation according to a second embodiment. In the configuration shown in FIG. 11, the readout circuit 523 in the configuration shown in FIG. 8 is removed, and a noise estimation section 508 and a noise removal and correction section 510 are provided. The noise estimation section 508 and the noise removal and correction section 510 executes a correction operation (base floating error correction) for reducing the base floating error (noise that causes the base floating).

That is, the noise estimation section 508 reads out the reception data S1 to S16 stored in the memory 506 and estimates a noise component (component having the wavelengths of a wavelength band w(≠m)) included in an interest reception signal (interest reception data) Sm based on the reception data S1 to S16.

Moreover, the noise removal and correction section 510 subtracts the sum of the noise components for each wavelength band from the interest reception signal (interest reception data) Sm to calculate a corrected reception signal (corrected reception data or corrected reception light intensity data). The signal processing section 600 executes predetermined signal processing based on the corrected reception signal (corrected reception data) corrected by the correction operation section 500 to calculate a spectrophotometric distribution, for example. The signal processing section 600 outputs a signal (that is, spectrophotometric distribution information) Sout representing the calculated spectral intensities for each wavelength.

Estimation of Noise Components

Among the plurality of wavelength bands (the first to n-th wavelengths, for example, n=16), the m-th wavelength band (1≤m≤n) will be referred to as an interest wavelength band. The interest wavelength band is a wavelength band that is being focused on in the correction processing of the reception data. Moreover, the k-th wavelength band (k≠m and 1≤k≤n) other than the m-th wavelength band will be referred to as a non-interest wavelength band.

The light receiving section 400 shown in FIG. 11 receives the transmission light or the reflection light of the m-th band-pass filter PDm and outputs an interest reception signal Sm (any one of S1a to S16a). Similarly, the light receiving section 400 receives the transmission light or reflection light of the k-th band-pass filter and outputs non-interest reception signals Sk (signals excluding the interest reception signal Sm from S1a to S16a).

Moreover, the transmittance or the reflectance in the k-th wavelength band of the m-th band-pass filter will be denoted as P(m,k), and the transmittance or the reflectance in the k-th wavelength band of the k-th band-pass filter will be denoted as P(k,k). Furthermore, the noise component for each wavelength band of the k-th wavelength band included in the interest reception signal Sm will be denoted as N(m,k).

Here, the noise estimation section 508 performs an operation based on Formula (1) below to estimate the amount of the noise components for each wavelength band of the k-th wavelength band included in the interest reception signal Sm.

$$N(m,k) = Sk \cdot \{P(m,k)/P(k,k)\} \quad (1)$$

Moreover, the noise removal and correction section 510 calculates the sum ΣN(m,k) of the estimated amount of noise components N(m,k) for each wavelength band. Moreover, the noise removal and correction section 510 performs an operation based on Formula (2) below to obtain a corrected reception signal (corrected reception data) Smc.

$$Smc = Sm - \Sigma N(m,k) \quad (2)$$

In Formula (1) above (that is, N(m,k)=Sk·{P(m,k)/P(k,k)}), Sk is the non-interest reception signals obtained by the light receiving section receiving the transmission light or the reflection light of the k-th band-pass filter. The non-interest reception signals are all of the reception signals which are the entire output of the photodiodes and are known since they are actually measured. Here, although it is ideal to use only the value of a reception signal corresponding to light of the k-th wavelength band among the non-interest reception signals, since it is not possible to separate only the reception component corresponding to the light of the k-th wavelength band, all of the reception signals of the k-th band-pass filter are used as a substitute.

Moreover, P(m,k) is the transmittance or the reflectance in the k-th wavelength band of the m-th band-pass filter. The notation P(m,k) represents the transmittance (or the reflectance) P in the "k"-th wavelength band which is the non-interest wavelength band, of the "m"-th band-pass filter (an optical filter associated with the "m"-th wavelength band which is the interest wavelength). Moreover, the spectral properties (relative spectral intensities of the respective wavelengths) in the all of the wavelength bands of the m-th band-pass filter are known.

Moreover, P(m,k) can be calculated by integrating the transmittance (reflectance) of the respective wavelengths included in the k-th wavelength band (that is, by calculating the entire area of the k-th wavelength band in a graph showing the relationship between wavelengths and transmittance (reflectance)). Therefore, P(m,k) is known.

Moreover, P(k,k) is the transmittance or the reflectance in the k-th wavelength band of the k-th band-pass filter. The notation P(k,k) represents the transmittance (or the reflectance) P in the "k"-th wavelength band which is the non-interest wavelength band, of the "k"-th band-pass filter (an optical filter associated with the "k"-th wavelength band which is the non-interest wavelength). Moreover, since the k-th band-pass filter is a filter associated with the k-th wavelength band, the transmittance in the k-th wavelength band is known.

The interest reception signal Sm is calculated using these known values. That is, the noise components N(m,k) for each wavelength band of the k-th wavelength band included in all of the reception signals obtained by the light receiving section receiving light from the m-th band-pass filter which is a filter associated with the interest wavelength band are calculated. The use of the expression "noise components N(m,k) for each wavelength band of the k-th wavelength band" is based on the following reason. As described above, the first to n-th wavelength bands are wavelength bands each having a predetermined wavelength width, and if n≥3, there will be two or more k-th wavelength bands which are the non-interest wavelength bands. Considering this, the expression expresses a case in which when there is a plurality of wavelength bands as the non-interest wavelength bands, the noise components for each wavelength band are calculated.

Here, it is possible to obtain the reception signal Sk corresponding to the transmittance (reflectance) P(k,k) in the k-th wavelength band of the k-th band-pass filter. That is, all of the reception signals can be taken to be a substitute by regarding them as the reception signal corresponding to the k-th wavelength band. If P(k,k) is changed to P(m,k), since the amount of reception signals changes in accordance with the ratio between P(k,k) and P(m,k), the amount of reception signals will be changed to Sk·{P(m,k)/P(k,k)}. This amount of reception signal is regarded as the noise components N(m,k) for each wavelength band of the k-th wavelength band included in the interest reception signal Sm. Formula (1) above expresses this.

In this way, when the noise components are calculated for each non-interest wavelength band, the noise removal and correction section 510 calculates the sum ΣN(m,k) of the estimated noise components N(m,k) for each wavelength band. The notation ΣN(m,k) represents the entire signal components (that is, all of the noise components ΣN) of the "k"-th wavelength band which is the non-interest wavelength band, included in all of the reception signals obtained by the light receiving section receiving light from the "m"-th band-pass filter which is a filter associated with the interest wavelength band.

Moreover, the noise removal and correction section 510 executes an operation based on Formula (2) (namely, Smc=Sm−ΣN(m,k)) to obtain the corrected reception signal Smc. The corrected reception signal Smc is obtained by removing noise therefrom and can be regarded as substantially the reception signal (reception data) corresponding to light of the interest wavelength band. Thus, the measurement accuracy of the optical spectrum data is improved.

More preferably, the noise estimation section 508 performs an operation based on Formula (3) below to estimate the amount of the noise components for each wavelength bands of the k-th wavelength band included in the interest reception signal Sm.

$$N(m,k) = Sk \cdot \{P(m,k)/P(k,k)\} \cdot R \quad (3)$$

In Formula (3) above, ΣQm(1~n) is the sum of the transmittance or the reflectance of the all of the wavelength bands of the m-th band-pass filter, and ΣQk(1~n) is the sum of the transmittance or the reflectance of all of the wavelength bands of the k-th band-pass filter. Moreover, R(=ΣQm(1~n)/ΣQk (1~n) is a correction coefficient for correcting the difference (or the difference in the total light intensity) in the transmittance property or the reflectance property between the respective band-pass filters. When calculating the noise components, by using Formula (3) in place of Formula (1) described above, it is possible to further increase the accuracy of noise estimation.

In the operation based on Formula (1) described above, noise components are calculated based on a way of thinking in which "if P(k,k) is changed to P(m,k), since the amount of reception signals changes in accordance with the ratio between P(k,k) and P(m,k), the amount of reception signals will be changed to Sk·{P(m,k)/P(k,k)}". However, actually, when an optical filter being used is switched from the k-th band-pass filter to the m-th band-pass filter, there is a difference in the total amount (total light intensity) of light entering the light receiving section after passing through the respective filters due to the different properties (for example, relative transmittance distribution or relative reflectance distribution) of the respective filters.

As described above, Sk used in Formula (1) above represents all of the reception signals of the light receiving section when the k-th band-pass filter is used. The noise components that are to be calculated are noise components included in all of the reception signals of the light receiving section when the m-th band-pass filter is used. That is, the noise components included in all of the reception signals when the m-th band-pass filter is used are estimated using actual measurement values when the k-th band-pass filter (a filter different from the m-th band-pass filter associated with correction) is used. At that time, there is a difference in the total amount (total light intensity) of light entering the light receiving section after passing through the respective filters due to the different properties (for example, relative transmittance distribution or relative reflectance distribution) of the respective filters. Therefore, by adding signal processing for compensating for the difference in the total light intensity resulting from the different properties of the respective filters when estimating noise, it is possible to further improve the measurement accuracy of the optical spectrum data.

Therefore, in the operation based on Formula (3) above, the operational formula of Formula (1) is multiplied by the correction coefficient R for correcting the difference in the transmittance property or the reflectance property between the filters.

Here, the sum of the transmittance or the reflectance of all of the wavelength bands of the m-th band-pass filter is denoted as $\Sigma Qm(1\sim n)$, and the sum of the transmittance or the reflectance of all of the wavelength bands of the k-th band-pass filter is denoted as $\Sigma Qk(1\sim n)$. When the k-th band-pass filter is switched to the m-th band-pass filter, the total amount of light entering the light receiving section will change in accordance with $\Sigma Qm(1\sim n)/\Sigma Qk(1\sim n)$. Therefore, all of the reception signals Sk obtained from the light receiving section when the k-th band-pass filter is used will be corrected as $Sk \cdot \{\Sigma Qm(1\sim n)/\Sigma Qk(1\sim n)\}$ when the m-th band-pass filter is used.

The ratio $(\Sigma Qm(1\sim n)/\Sigma Qk(1\sim n))$ of the sum of transmittance properties and reflectance properties between the respective filters will be referred to as the correction coefficient R for correcting (compensating for) the difference in the transmittance properties or the reflectance properties between the respective filters. By multiplying the operational formula of Formula (1) above by the correction coefficient R, the difference in the transmittance properties or the reflectance properties between the respective filters is compensated. Accordingly, the measurement accuracy of the optical spectrum data is improved further.

A specific example of estimation of noise components is illustrated on the lower side of FIG. 11. In this example, it is assumed that a transmission-type optical band-pass filter is used as the optical band-pass filter section 300. Moreover, it is assumed that reception data S3 obtained by converting an analog reception signal S3a output from the third photodiode PD(3) into a digital value is used as an interest reception signal (interest reception data). In the reception data S3, noise components are superimposed for each wavelength band of w(1), w(2), and w(4) to w(16) which are non-interest wavelength bands. In the example of FIG. 11, it is assumed that the amount of the noise components in the 13th wavelength band (w(13)) is first estimated in accordance with Formula (3) described above.

The noise components in the 13th wavelength band (w(13)) included in the interest reception signal (interest reception data) S3 can be obtained by multiplying the non-interest reception signal (non-interest reception data) S13 by the transmittance (total light intensity) correction coefficient R between the third band-pass filter BPF(3) and the 13th band-pass filter BPF(13) and multiplying the same by the ratio (P(3,13)/P(13,13)) of the transmittances of the 13th wavelength band (w(13)) in the respective filters.

The correction coefficient R can be calculated by Fbps3 ($\lambda$=380~780)/Fbps13($\lambda$=380~780). Here, Fbps3 ($\lambda$=380~780) is an integrated value of the transmittances of the respective 16 wavelength bands in the third band-pass filter BPF(3). Moreover, Fbps13($\lambda$=380~780) is an integrated value of the transmittances of the respective 16 wavelength bands in the 13th band-pass filter BPF(13).

Moreover, Fbps3($\lambda$=640) (=P(m,k)=P(3,13)) is a transmittance in the 13th wavelength band w(13) (central wavelength: 640 nm) of the third band-pass filter BPF(3). Furthermore, Fbps13($\lambda$=640) (=P(k,k)=P(13,13)) is a transmittance in the 13th wavelength band w(13) (central wavelength: 640 nm) of the 13th band-pass filter BPF(13).

Since components (noise components) of unnecessary wavelength bands, which are superimposed on the reception data (reception light intensity data) are removed by such a correction operation, the accuracy of the reception data (reception light intensity data) is improved. Therefore, it is possible to improve the measurement accuracy of a spectral measurement device without using an optical band-pass filter which is expensive and large.

The corrected reception data in which the base floating error is reduced are stored in the memory 506. When performing the integration error correction, it is preferable to use the reception data in which the base floating error is reduced as the basic data for calculating the second derivative. This is because a more accurate second derivative can be obtained when the second derivative is calculated based on the actual measurement data in which the noise is reduced (that is, the change in the spectral reflectance can be detected more accurately).

Figure 12A:
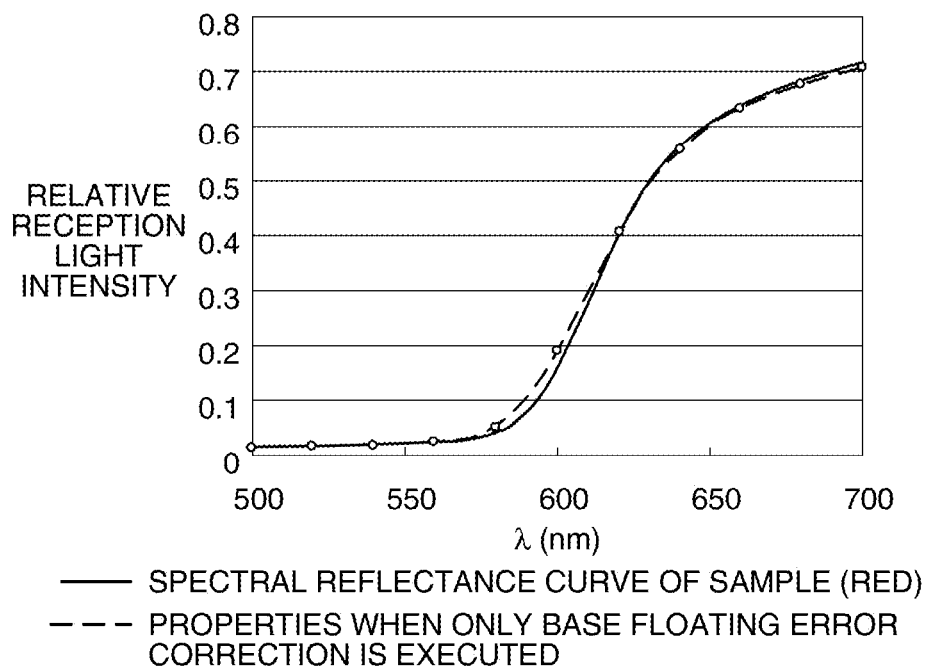
FIGS. 12A and 12B are diagrams illustrating the effect of base floating correction.
Figure 12B:
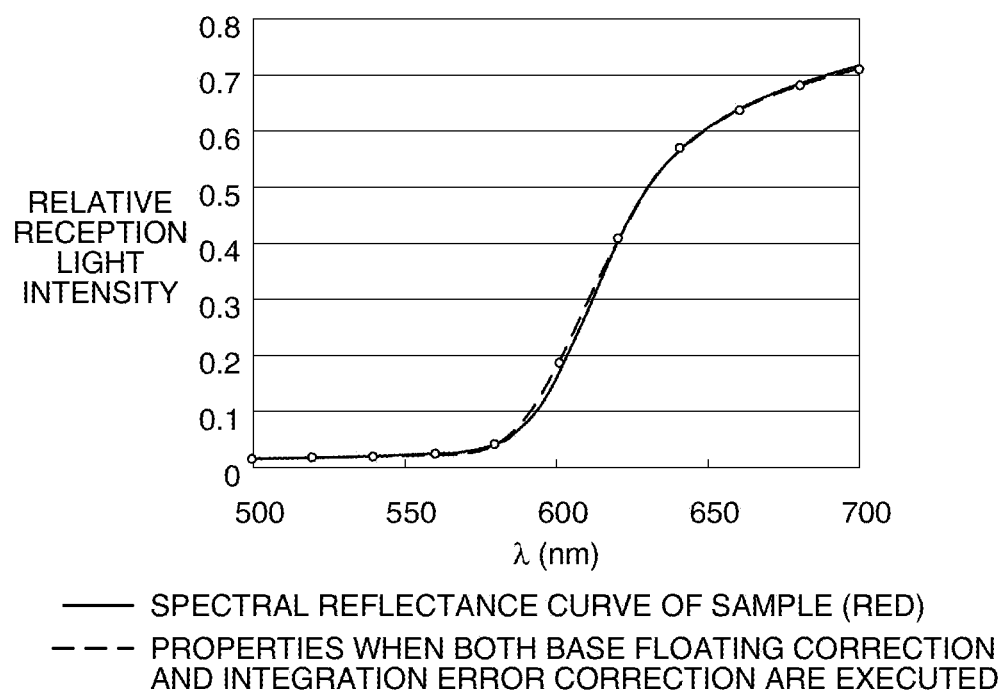

FIGS. 12A and 12B are diagrams illustrating the effect of base floating correction. FIG. 12A shows spectral distribution properties when only the base floating error correction is executed, and FIG. 12B shows spectral properties when both the base floating error correction and the integration error correction (correction of errors in the reflectance changing region) are used. FIGS. 12A and 12B show the spectral distribution curve and the spectral distribution (in this example, a spectral reflectance distribution) of the sample which are generated based on the corrected 16-point data (the surface color of the sample being used is red). The spectral reflectance obtained based on the corrected measurement data (16-point data) is indicated by white circles. The actual spectral reflectance distribution of the sample (red) is indicated by a solid line.

As shown in FIG. 12A, the measurement data in the wavelength band of 400 nm to 560 nm are substantially identical to the actual spectral reflectance distribution of the sample (red). However, as described earlier in FIG. 4, an error (integration error) occurs in a spectral reflectance changing region in the vicinity of the wavelengths 580 nm to 700 nm.

In the example of FIG. 12B, since the integration error correction is also executed in addition to the base floating error correction, the measured spectral reflectance values in the vicinity of the wavelengths 580 nm to 700 nm are substantially identical to the actual spectral reflectance values of the sample (red). In this way, according to the present embodiment, since both the base floating error and the integration error are reduced, higher accuracy spectral measurement is possible.

Specific Example of Base Floating Error Correction

Figure 13A:
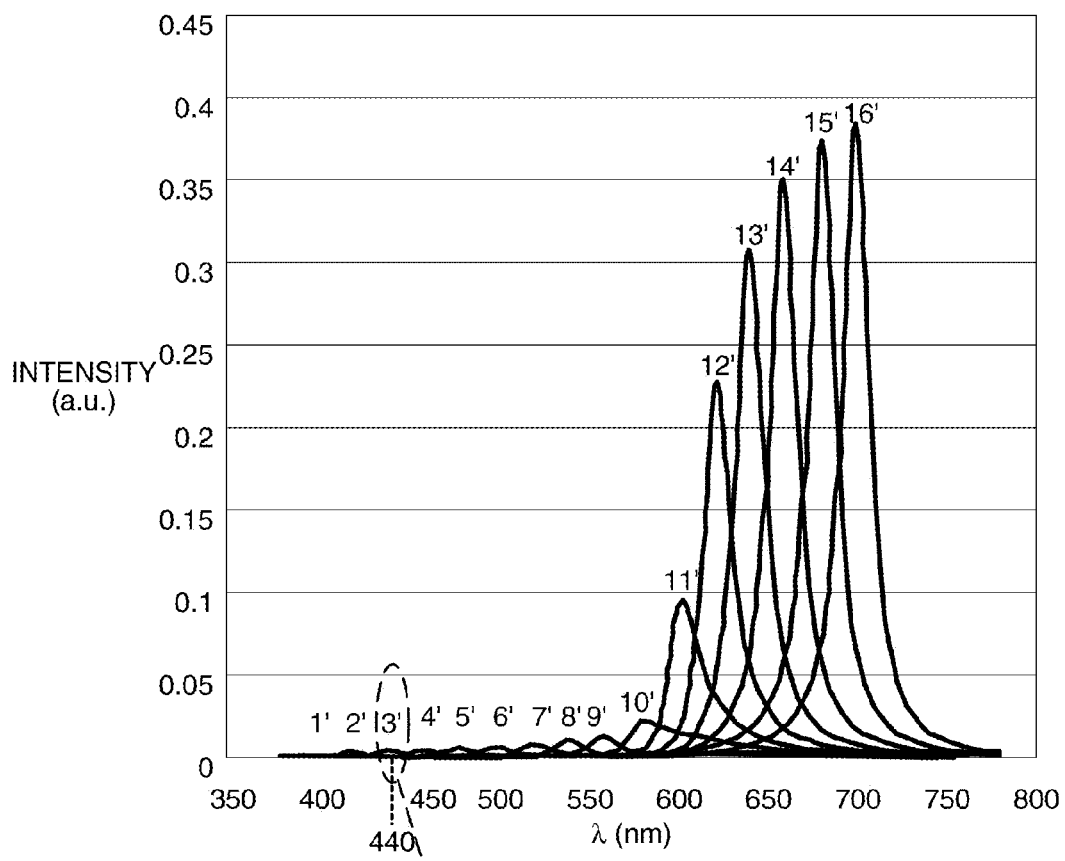
FIGS. 13A and 13B are diagrams showing the distribution of reception signal intensities (relative reception signal intensities) of respective photodiodes and showing the extracted optical spectra of a reception signal in a third wavelength band (a wavelength band having a central wavelength of 440 nm) in an enlarged scale, respectively.
Figure 13B:
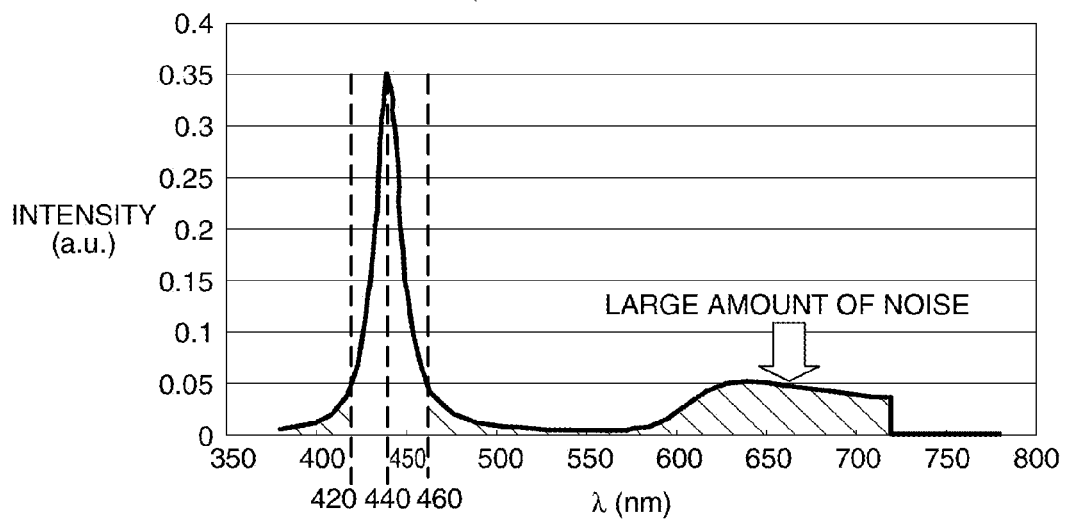

Next, base floating error correction will be described in detail. FIGS. 13A and 13B are diagrams showing the distribution of reception signal intensities (relative reception signal intensities) of respective photodiodes of the light receiving section and showing the extracted optical spectra of a reception signal in a third wavelength band (a wavelength band having a central wavelength of 440 nm) in an enlarged scale, respectively. The reception signals of each of the first to 16th photodiodes PD(1) to PD(16) are denoted as 1', 2', . . . , and 16'. Since the surface color of the sample is red, the reception signal intensities in the first to 10th wavelength bands are not higher than the reception signal intensities in the 11th to 16th wavelength bands. Therefore, large noise components are superimposed on the first to 10th wavelength bands to cause base floating. Thus, the S/N ratio of the reception signals in these respective wavelength bands decreases greatly.

FIG. 13B shows the extracted optical spectra of the reception signal 3' in the third wavelength band in an enlarged scale. Since the half bandwidth of the third band-pass filter BPF(3) is broad, the components of the respective first, second, and fourth to 16th wavelength bands in addition to the wavelength components of the third wavelength band which is the original wavelength band are superimposed on the reception signal 3'. Since the material color (surface color) of the sample 200 is red, large noise components (unnecessary components) appear in the vicinity of a wavelength band of 600 nm to 720 nm.

Therefore, base floating error correction is executed. In this way, most of the noise components superimposed on the reception signal 3' in the third wavelength band are removed, and the accuracy of the measurement signals in the third wavelength band is improved. The same correction processing is executed on the other wavelength bands (particularly, a wavelength band of 600 nm or lower in which base floating is likely to occur).

Next, correction of data in a colorimeter (color measurement device) will be described in detail with reference to FIGS. 14A to 19B. FIGS. 14A and 14B are diagrams illustrating an outline of an estimation method of noise components in a 13-th wavelength band, which are included in the light of a third wavelength band passed through a third band-pass filter.

For example, although the third band-pass filter BPF(3) is an optical filter associated with a wavelength band having a width of 20 nm and a central wavelength of 440 nm, as described above, since the actual reception signal of the third photodiode (third photoreceiver) PD(3) includes the components (noise components) of the other wavelength bands (the first, second, and fourth to 16th wavelength bands). In order to correct the reception data, it is necessary to estimate the signal amount of the noise components in the respective wavelength bands.

In FIG. 14A, a wavelength band having a central wavelength of 440 nm indicated by a reticular pattern is the original wavelength associated with the third band-pass filter BPF(3). In this example, a case of estimating the amount of the noise components indicated by hatching among the noise components (FIG. 14A) of the 13th wavelength band will be described as an example.

In estimation of the amount of the noise components of the 13th wavelength band, some basic data are required. As the basic data, the reception data obtained by the 13th photodiode PD(13) receiving light having passed through the 13th band-pass filter BPF(13) are used. It may be ideal to use only the reception data of the 13th wavelength band indicated by a dotted pattern in FIG. 14B as the basic data. However, since it is not possible to know only the amount of reception signal of the 13th wavelength band among all of the reception signals of the 13th photodiode PD(3), all of the reception signals obtained from the 13th photodiode PD(3) (that is, the reception data indicated by hatching in FIG. 14B) are used (substituted) in place of the reception data of the 13th wavelength band.

The reception signal intensity of the 13th wavelength band corresponding to the third photodiode PD(3) shown in FIG. 14A is lower than the reception signal intensity of the 13th wavelength band corresponding to the 13th photodiode PD(13) shown in FIG. 14B. However, this is because the transmittance of the third band-pass filter BPF(3) in the 13th wavelength band is different from the transmittance of the 13th band-pass filter BPF(13) in the 13th wavelength band. If the difference in the transmittance between the respective filters is known, by multiplying the reception signal intensity (substituted by entire reception data) of the 13th wavelength band corresponding to the 13th photodiode PD(13) by the ratio of transmittance between the respective filters in the 13th wavelength band, it is possible to estimate the amount of the noise components (the reception signal intensity of the 13th wavelength band corresponding to the third photodiode PD(3)).

FIGS. 15A to 15D are diagrams showing a first specific example (correction using Operational Formula (1)) of a method of estimating the amount of the noise components. In FIG. 15A, signal components indicated by a dotted pattern are reception signal components (unclear) in the 640 nm band (the 13th wavelength band w(13)) of the 13th band-pass filter BPF(13) (a band-pass filter associated with the 640 nm band). In place of the reception signal components, all of the reception signals $Ix(\lambda=640$ nm) of the 13th photodiode PD(13) shown in FIG. 15C are substituted. All of the reception signals $Ix(\lambda=640$ nm) of the 13th photodiode PD(13) are the integrated value of detection current for each wavelength of the 13th photodiode PD(13). All of the reception signals are known since they are actually measured.

Moreover, the transmittance (Fbps13($\lambda=640$)) in the 640 nm band (the 13th wavelength band w(13)) of the 13th band-pass filter BPF(13) is known. That is, the transmittance property is already known since the transmittance is the transmittance of the original band of the 13th band-pass filter BPF(13).

Moreover, in FIG. 15B, signal components indicated by hatching are noise components which are to be estimated. The noise components are reception signal components (unknown) in the 440 nm band (the 13th wavelength band w(13)) of the third band-pass filter BPF(3) (a band-pass filter associated with the 440 nm band). In the drawing, the noise components are denoted as c1x1(440,640). This notation represents the noise components c1x1 in the 640 nm band of a band-pass filter associated with the 440 nm band.

However, the transmittance (Fbps3($\lambda=640$)) in the 640 nm band (the 13th wavelength band w(13)) of the third band-pass filter BPF(3) is known. That is, Fbps3($\lambda=640$) can be calculated by integrating the transmittances Fbps($\lambda$630) to Fbps($\lambda$650) in the respective wavelength bands of 630 nm to 650 nm of the third band-pass filter BPF(3) and then averaging the integrated value.

FIG. 15D shows the specific content of the correction operational formula (Formula (1)) described above. That is, specifically, Formula (1) can be expressed as follows.

$$\text{Noise Component } c1x1(440,640) \approx Ix(\lambda=640 \text{ nm}) \times Fbps(\lambda=640)/Fbps13(\lambda=640) \quad (1)$$

FIGS. 16A to 16C are diagrams showing a second specific example (correction using Operational Formula (3)) of a method of estimating the amount of the noise components. In Formula (1) described above, the difference in transmittance (difference in total light intensity) between the filters is not taken into consideration. Therefore, in the example shown in FIGS. 16A to 16C, the basic data serving as the basis of noise estimation are corrected using the correction coefficient (transmittance correction coefficient) R for correcting the difference in transmittance (difference in total light intensity) between the filters.

"Fbps3($\lambda$=380~780)" shown in FIG. 16A is an integrated value of the transmittances in the respective 16 wavelength bands w(1) to w(16) of the third band-pass filter BPF(3). Similarly, "Fbps13($\lambda$=380~780)" shown in FIG. 16B is an integrated value of the transmittances in the respective 16 wavelength bands w(1) to w(16) of the 13th band-pass filter BPF(13).

"Fbps3($\lambda$=380~780)" corresponds to an integrated value of detection current for each wavelength of the third photodiode PD(3); that is, it corresponds to the total area of a closed figure determined by an optical spectrum distribution curve. Moreover, "Fbps13($\lambda$=380~780)" corresponds to an integrated value of detection current for each wavelength of the 13th photodiode PD(13); that is, it corresponds to the total area of a closed figure determined by an optical spectrum distribution curve. By comparing the area of a closed figure shown in FIG. 16A and the area of a closed figure shown in FIG. 16B, it is possible to know that the two areas are different (this results from a difference in optical spectrum properties). That is, the total intensities of light after passing through the respective band-pass filters are different.

Therefore, in the operation based on Formula (3), the basic data Ix($\lambda$=640 nm) serving as the basis of noise estimation are corrected considering the difference in transmittance (difference in total light intensity) between the filters. That is, as shown in FIG. 16C, all of the reception signals Ix($\lambda$=640 nm) are multiplied by the correction coefficient R (transmittance correction coefficient) representing the ratio of transmittances in the all of the wavelength bands of the respective filters, and all of the reception signals Ix($\lambda$=640 nm) of the 13th photodiode PD(13) are corrected so as to correspond to the properties of the third band-pass filter BPF(3).

The data obtained through correction are used as the basic data for noise estimation, and the corrected basic data are multiplied by the ratio (Fbps($\lambda$=640)/Fbps13($\lambda$=640)) of transmittances in the 13th wavelength band of the respective filters to thereby calculate the noise component c1x1(440, 640) of the 13th wavelength band included in the reception signal (third reception data) of the third photodiode PD(3). This is the content of Formula (3) shown in FIG. 16C. According to Formula (3), since the basic data are corrected considering the difference in optical properties (transmittance or reflectance) between the filters, the measurement accuracy is further improved.

After that, the amounts of the noise components in the respective first, second, fourth to 12th, and 14th to 16th wavelength bands included in the reception signal (third reception data) obtained from the third photodiode PD(3) are estimated by the same method (correction operation based on Formula (1) or (3)). The estimated noise data of the respective wavelength bands are temporarily stored in the memory 506.

FIGS. 17A to 17C are diagrams illustrating the content of noise removal and correction by a noise removal and correction section 510. As shown in FIG. 17A, the noise removal and correction section 510 calculates the third reception data corresponding to the third band-pass filter BPF(3). That is, the noise removal and correction section 510 calculates the sum (c1x1(440)) of noise components included in the reception data obtained from the third photodiode PD(3). Here, the notation c1x1(440) represents all of the noise components c1x1 included in the reception data of the 440 nm band.

FIG. 17B shows all of the reception signals (the integrated value of detection current for each wavelength) Ix($\lambda$=640 nm) of the 13th photodiode. All of the reception signals Ix($\lambda$=640 nm) can be calculated accurately by a mathematical formula. That is, when $\lambda$1 is used as a parameter representing the wavelength of light, Ix($\lambda$=640 nm) can be calculated by integrating the products of an actual light source ($\lambda$1), a filter transmittance ($\lambda$1), a PD spectral sensitivity ($\lambda$1), a sample spectral reflectance ($\lambda$1), and a transmittance in $\lambda$1 of the BPF(3) over a range of $\lambda$1 from 380 to 700.

The noise removal and correction section 506 subtracts the calculated sum (c1x1(440)) of the noise components from all of the reception signals (integrated value of detection current for each wavelength) Ix($\lambda$=640 nm) of the 13th photodiode (this subtraction corresponds to an operation based on Formula (2) above). In this way, as shown in FIG. 17C, it is possible to obtain a detection signal (the third reception data after correction) of the 440 nm band in which noise components are greatly suppressed. The same correction processing is executed for the reception data of the other wavelength bands.

Figure 18A:
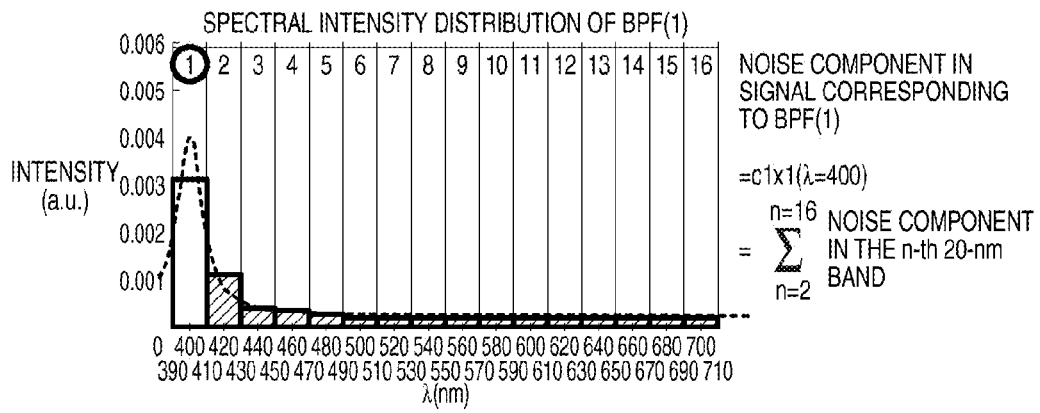
FIGS. 18A to 18C are diagrams showing an example of a method of calculating the sum of the noise components.
Figure 18B:
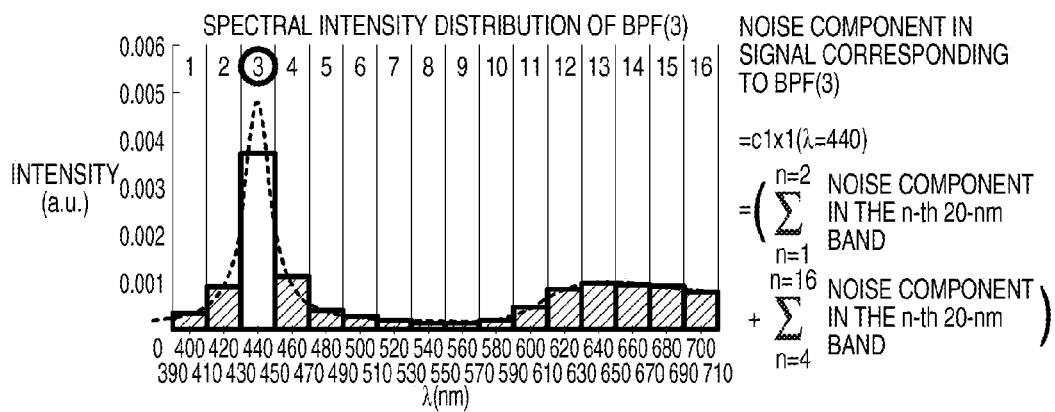
Figure 18C:
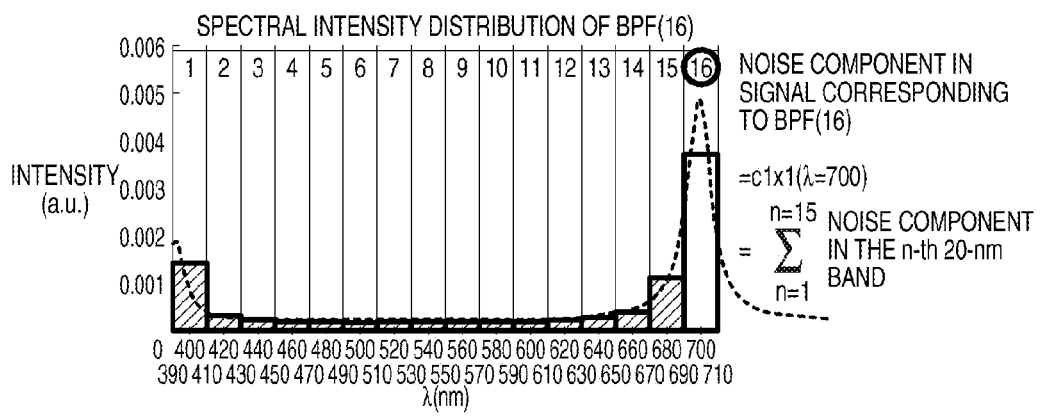

FIGS. 18A to 18C are diagrams showing an example of a method of calculating the sum of the noise components. When there are the first to n-th wavelengths (n is an integer of 2 or more, and in this example, n=16) having a predetermined wavelength width (in this example, width=20 nm) as a spectral band, three methods shown in FIGS. 18A to 18C can be considered as a method of calculating the sum of the noise components included in the m-th reception data which are the interest reception data (here, the sum corresponds to the sum of the noise components in the k-th wavelength band (k$\neq$m and 1$\leq$k$\leq$n) which is the non-interest wavelength).

In the case of FIG. 18A, the first wavelength band is the interest wavelength band, and the second to 16th wavelength bands are the non-interest wavelength bands. Therefore, the sum c1x1($\lambda$=400) of noise components can be calculated by summing the noise components in the respective second to 16th wavelength bands.

In the case of FIG. 18B, the third wavelength band is the interest wavelength band, for example, and the respective first, second, and fourth to 16th wavelength bands are the non-interest wavelength bands. Therefore, the sum c1x1 ($\lambda$=440) of noise components can be calculated by adding the sum of the noise components in the respective first and second wavelength bands and the sum of the noise components in the respective fourth to 16th wavelength bands.

In the case of FIG. 18C, the 16th wavelength band is the interest wavelength band, and the first to 15th wavelength bands are the non-interest wavelength bands. Therefore, the sum c1x1($\lambda$=700) of noise components can be calculated by summing the noise components in the respective first to 15th wavelength bands.

Figure 19A:
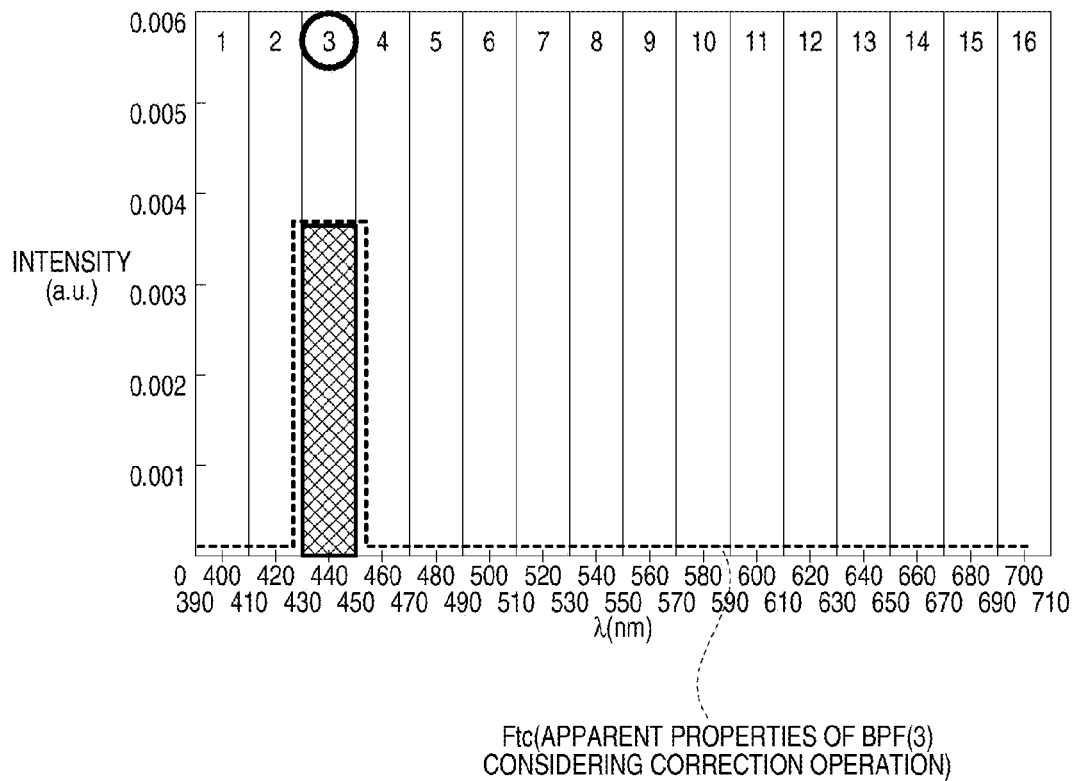
FIGS. 19A and 19B are diagrams showing a difference in the band-pass filter properties depending on the presence of correction processing.
Figure 19B:
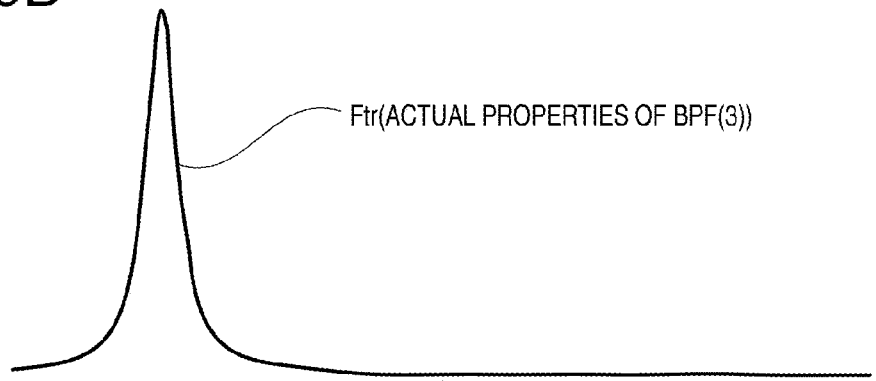

FIGS. 19A and 19B are diagrams showing a difference in the band-pass filter properties depending on the presence of a correction process. As shown in FIG. 19B, the actual spectral property Ftr of the optical band-pass filter section 300 has a property such that it has broad skirts. However, when the reception data are corrected so as to suppress noise, the spectral property Ftc of the optical band-pass filter section 300 is changed to a steep band-pass property as shown in FIG. 19A. Therefore, it is possible to improve the measurement accuracy of the spectral measurement device while allowing the use of various optical filters. For example, high-accuracy spectral measurement can be performed using a simple and cheap wavelength band-pass filter such as a variable-gap etalon.

As described above, according to at least one embodiments of the invention, it is possible to improve the measurement accuracy of the spectral measurement device without using an expensive optical band-pass filter, for example.

Although some embodiments of the invention have been described above in detail, those skilled in the art will readily understand that various modifications may be made without substantially departing from the new items and the effects of the invention. Therefore, such modifications are entirely included within the scope of the invention. For example, any term described at least once together with a broader or synonymous different term in the specification or the drawing may be replaced by the different term at any place in the specification or the drawings. For example, even when two or more optical low-pass filters or two or more optical high-pass filters are used in place of the optical band-pass filter, the invention can be applied if the wavelengths of the transmission light (reflection light) overlap with each other.

Moreover, although in the embodiments described above, the spectral reflectance of a sample was used, the same problem occurs when spectral measurement is performed using an optical filter having a broad half bandwidth, for example, by calculating the transmittance or absorptance of a sample. Therefore, the invention can be applied to a case of calculating the spectral transmittance and the spectral absorptance of a sample. For example, a relation of (Reflectance)+(Absorptance)=1 and a relation of (Transmittance)+(Absorptance)=1 are satisfied. Therefore, the relations can be expressed as Absorptance=1−(Reflectance) and Transmittance=1−(Absorptance). Thus, if the spectral reflectance of a sample is known, the spectral absorptance and the spectral transmittance of the sample can be measured in accordance with the formulas above.

The invention can be broadly applied to spectral measurement devices such as a colorimeter, a spectroscopic analyzer, and an optical spectrum analyzer.

What is claimed is:

1. A method for measuring a spectral distribution using a spectral measurement device having an optical band-pass filter section, a light receiving section receiving light from the optical band-pass filter section and a correction operation section performing an operation to correct a reception signal obtained from the light receiving section, the method comprising the steps of:
(a) receiving light of first to n-th wavelengths, wherein n is an integer of 3 or more, by the light receiving section;
(b) calculating a second derivative of a characteristic line representing the spectral distribution of the reception signals of the light of first to n-th wavelengths by the correction operation section; and
(c) decreasing the reception signal when the second derivative is positive and increasing the reception signal when the second derivative is negative by the correction operation section.

2. The method according to claim 1, wherein,
a correction value used for the decreasing and increasing in step (c) is based on a magnitude of an absolute value of the second derivative.

3. The method according to claim 1, wherein
when a reception light intensity of a first spectral band is p1, a reception light intensity of a second spectral band adjacent to the first spectral band is p2, and a reception light intensity of a third spectral band adjacent to the second spectral band is p3, a second derivative Q1 is calculated through an operation based on Q1=(p1+p3−2·p2) and calculates a correction value used for correcting the reception light intensity p2 of the second spectral band by subtracting a product of the calculated second derivative Q1 and a correction coefficient k1, k1 is a real number, by the correction operation section in step (b).

4. The method according to claim 1, further comprising;
when, among the first to n-th wavelengths, an m-th wavelength band, wherein 1≤m≤n and m is an integer, is an interest wavelength band, and a k-th wavelength band, wherein k≠m, 1≤k≤n, and k is an integer, other than the m-th wavelength band is non-interest wavelength band, the optical band-pass filter section functions as an m-th band-pass filter corresponding to the m-th wavelength band and also functions as a k-th band-pass filter corresponding to the k-th wavelength band,
a step of estimating a noise component for each wavelength band of the k-th wavelength band included in an interest reception signal obtained by the light receiving section receiving transmission light or reflection light of the m-th band-pass filter corresponding to the m-th wavelength band by the correction operation section being done after step (a) and before step (b), wherein the estimating includes multiplying each wavelength band of the k-wavelength band included in the interest reception signal by a transmittance or a reflectance in the k-th wavelength band of the m-th band pass filter, and;
subtracting a sum of the estimated noise component for each wavelength band from the interest reception signal by the correction operation section after step (a) and before step (b).

5. The method according to claim 4, wherein
when the interest reception signal obtained by the light receiving section receiving the transmission light or reflection light of the m-th band-pass filter is Sm,
all of the reception signal obtained by the light receiving section receiving the transmission light or reflection light of the k-th band-pass filter is Sk,
a transmittance or a reflectance in the k-th wavelength band of the m-th band-pass filter is P(m,k),
a transmittance or a reflectance in the k-th wavelength band of the k-th band-pass filter is P(k,k), and
the estimated noise component for each wavelength band of the k-th wavelength band included in the interest reception signal Sm is N(m,k), wherein the N(m,k) is estimated by an operation based on Formula (1) below, $$N(m,k)=Sk\cdot\{P(m,k)/P(k,k)\} \quad (1),$$

and
a sum ΣN (m,k) of the estimated noise component N(m,k) for each wavelength band is calculated and the corrected reception signal Smc is obtained by an operation based on Formula (2) below, $$Smc=Sm-\Sigma N(m,k) \quad (2).$$

6. The method according to claim 5, wherein
when a sum of transmittance or reflectance of all of the wavelength bands of the m-th band-pass filter is EQm (1~n),
a sum of transmittance or reflectance of all of the wavelength bands of the k-th band-pass filter is EQk(1~n), and
a correction coefficient for correcting a difference in the transmittance properties or reflectance properties between filters is R(=ΣQm(1~n)/ΣQk(1~n)),
the estimated noise component for each wavelength band of the k-th wavelength band included in the interest reception signal Sm is estimated by an operation based on Formula (3) below, $$N(m,k) = Sk \cdot \{P(m,k)/P(k,k)\} \cdot R \qquad (3).$$

* * * * *